US012290599B2

(12) United States Patent
Burnam

(10) Patent No.: US 12,290,599 B2
(45) Date of Patent: *May 6, 2025

(54) OIL-BASED WOUND CARE COMPOSITIONS AND METHODS

(71) Applicant: GLOBAL HEALTH SOLUTIONS LLC, Rome, GA (US)

(72) Inventor: Bradley Burnam, Calabasas, CA (US)

(73) Assignee: GLOBAL HEALTH SOLUTIONS LLC, Rome, GA (US)

(*) Notice: Subject to any disclaimer, the term of this patent is extended or adjusted under 35 U.S.C. 154(b) by 104 days.

This patent is subject to a terminal disclaimer.

(21) Appl. No.: 17/020,567

(22) Filed: Sep. 14, 2020

(65) Prior Publication Data

US 2020/0405637 A1  Dec. 31, 2020

Related U.S. Application Data

(63) Continuation-in-part of application No. 16/917,846, filed on Jun. 30, 2020, now Pat. No. 10,966,927, which is a continuation of application No. 15/167,099, filed on May 27, 2016, now Pat. No. 10,722,461.

(60) Provisional application No. 62/182,034, filed on Jun. 19, 2015, provisional application No. 62/319,449, filed on Apr. 7, 2016, provisional application No. 62/326,150, filed on Apr. 22, 2016, provisional application No. 62/338,995, filed on May 19, 2016.

(51) Int. Cl.
| | |
|---|---|
| *A61K 9/10* | (2006.01) |
| *A61K 8/00* | (2006.01) |
| *A61K 8/04* | (2006.01) |
| *A61K 8/31* | (2006.01) |
| *A61K 9/00* | (2006.01) |
| *A61K 9/06* | (2006.01) |
| *A61K 31/785* | (2006.01) |
| *A61K 38/18* | (2006.01) |
| *A61K 38/20* | (2006.01) |
| *A61K 45/06* | (2006.01) |
| *A61K 47/06* | (2006.01) |
| *A61Q 19/00* | (2006.01) |

(52) U.S. Cl.
CPC ............. *A61K 9/10* (2013.01); *A61K 8/00* (2013.01); *A61K 8/044* (2013.01); *A61K 8/31* (2013.01); *A61K 9/0014* (2013.01); *A61K 9/06* (2013.01); *A61K 31/785* (2013.01); *A61K 38/1825* (2013.01); *A61K 38/1841* (2013.01); *A61K 38/20* (2013.01); *A61K 45/06* (2013.01); *A61K 47/06* (2013.01); *A61Q 19/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 2,640,801 A | 6/1953 | Burkhart et al. | |
| 4,895,452 A | 1/1990 | Yiournas et al. | |
| 5,466,463 A | 11/1995 | Ford | |
| 5,994,300 A | 11/1999 | Bayne et al. | |
| 6,106,855 A | 8/2000 | Haynes et al. | |
| 6,248,338 B1 | 6/2001 | Müller et al. | |
| 6,309,664 B1 | 10/2001 | Mathur et al. | |
| 7,074,459 B2 | 7/2006 | Stockel | |
| 7,365,200 B2 | 4/2008 | Sircar et al. | |
| 8,323,674 B2 | 12/2012 | Antoni-Zimmermann et al. | |
| 10,675,243 B2 | 6/2020 | Burnam | |
| 10,722,461 B2 | 7/2020 | Burnam | |
| 10,874,608 B2 | 12/2020 | Burnam | |
| 10,966,927 B2 | 4/2021 | Burnam | |
| 11,565,020 B2 | 1/2023 | Burnam | |
| 2002/0146440 A1 | 10/2002 | Smith | |
| 2003/0012741 A1 | 1/2003 | Furlan et al. | |
| 2005/0019431 A1 | 1/2005 | Modak et al. | |
| 2005/0048020 A1 | 3/2005 | Willie | |
| 2006/0051385 A1 | 3/2006 | Scholz | |
| 2007/0020213 A1* | 1/2007 | Tamarkin | A61K 47/14 424/70.1 |
| 2007/0048345 A1 | 3/2007 | Huang et al. | |
| 2007/0141091 A1 | 6/2007 | Xia et al. | |
| 2008/0279944 A1 | 11/2008 | Sawhney | |
| 2008/0287336 A1 | 11/2008 | Patel et al. | |

(Continued)

FOREIGN PATENT DOCUMENTS

| | | |
|---|---|---|
| CN | 1771937 A | 5/2006 |
| CN | 103182070 A | 7/2013 |

(Continued)

OTHER PUBLICATIONS

European Search Report; European Application No. 16812129.1; mailed Feb. 22, 2019.
Supplementary European Search Report; European Application No. 16812128.3; mailed Mar. 12, 2019.
Hwang, Chiaw-Chi et al., Percutaneous Absorption of Flufenamic Acid in Rabbits; Effect of Dimethyl Sulfoxide and Various Nonionic Surface-Active Agents; Journal of Pharmaceutical Association, U.S., vol. 72, No. 8, Aug. 1983, pp. 857-860.

(Continued)

*Primary Examiner* — David J Blanchard
*Assistant Examiner* — Sarah J Chickos
(74) *Attorney, Agent, or Firm* — Womble Bond Dickinson (US) LLP

(57) ABSTRACT

Compositions and methods for wound care or the dressing or treatment of wounds in a subject in need thereof. The compositions include an oil-based carrier, a polar solvent comprising one or more polar antimicrobial agents, and collagen or a collagen-based material. In at least some instances, the polar solvent comprising the one or more polar antimicrobial agents and the collagen or collagen-based material are suspended in the oil-based carrier.

20 Claims, No Drawings

(56) References Cited

U.S. PATENT DOCUMENTS

| | | |
|---|---|---|
| 2009/0136435 A1 | 5/2009 | Mulvanerty |
| 2009/0162304 A1 | 6/2009 | DiLeva |
| 2009/0269394 A1 | 10/2009 | Baker, Jr. et al. |
| 2009/0281013 A1 | 11/2009 | Patel et al. |
| 2010/0092526 A1 | 4/2010 | Baker, Jr. et al. |
| 2010/0203139 A1 | 8/2010 | Baker, Jr. et al. |
| 2010/0226983 A1 | 9/2010 | Sutcliffe et al. |
| 2010/0233224 A1 | 9/2010 | Ramadurai et al. |
| 2011/0002820 A1 | 1/2011 | Dawson et al. |
| 2011/0052656 A1 | 3/2011 | Whitekettle et al. |
| 2011/0251285 A1 | 10/2011 | Tien et al. |
| 2013/0011342 A1* | 1/2013 | Tamarkin ............... A61P 29/00 514/172 |
| 2013/0150765 A1 | 6/2013 | Moghe et al. |
| 2014/0234419 A1 | 4/2014 | McAnulty et al. |
| 2014/0248219 A1 | 9/2014 | Tamarkin et al. |
| 2014/0276493 A1* | 9/2014 | Leung ..................... A61L 15/46 424/641 |
| 2016/0106674 A1 | 4/2016 | Scalesciani |
| 2016/0206567 A1 | 7/2016 | Ridden et al. |
| 2016/0367504 A1 | 12/2016 | Burnam |
| 2016/0367676 A1 | 12/2016 | Burnam |
| 2017/0232004 A1 | 8/2017 | Genberg et al. |
| 2017/0333346 A1 | 11/2017 | Burnam |
| 2017/0354754 A1 | 12/2017 | Liden et al. |
| 2018/0008711 A1 | 1/2018 | Selner |
| 2018/0036236 A1 | 2/2018 | Selner |
| 2019/0015548 A1 | 1/2019 | Harrell |
| 2020/0268660 A1 | 8/2020 | Burnam |
| 2020/0330381 A1 | 10/2020 | Burnam |
| 2020/0397869 A1 | 12/2020 | Leung et al. |
| 2020/0405637 A1 | 12/2020 | Burnam |
| 2021/0186874 A1 | 6/2021 | Burnam |
| 2022/0249734 A1 | 8/2022 | Burnam |

FOREIGN PATENT DOCUMENTS

| | | | |
|---|---|---|---|
| EP | 1872788 A1 | | 1/2008 |
| WO | WO2005053617 | * | 6/2005 |
| WO | 2006099359 A2 | | 9/2006 |
| WO | WO 2013/183770 | * | 5/2013 |
| WO | 2013186766 A1 | | 12/2013 |
| WO | 2014183770 A1 | | 11/2014 |
| WO | 2015118069 A1 | | 8/2015 |
| WO | 2016126982 A1 | | 8/2016 |
| WO | 2018226479 A1 | | 12/2018 |

OTHER PUBLICATIONS

Fuchs, T. et al., "Benzalkoniumchlorid-relevantes Kontaktallergen order Irritans?, Benzalkonium chloride—a relevant contact allergen or irritant?, Results of a multicenter study of the German Contact Allergy Group"I Hautartz, Springer Verlag, Berlin, DE, vol. 44, No. 11, Nov. 1993, pp. 699-702.

* cited by examiner

OIL-BASED WOUND CARE COMPOSITIONS AND METHODS

CROSS-REFERENCE TO RELATED APPLICATIONS

This application is a Continuation-In-Part of U.S. application Ser. No. 16/917,846, filed Jun. 30, 2020, which is a continuation of U.S. application Ser. No. 15/167,099, filed May 27, 2016, which is now issued as U.S. Pat. No. 10,722,461, and which claims benefit of priority to U.S. Provisional Application Ser. No. 62/182,034, filed Jun. 19, 2015, U.S. Provisional Application Ser. No. 62/319,449, filed Apr. 7, 2016, U.S. Provisional Application Ser. No. 62/326,150, filed Apr. 22, 2016, and U.S. Provisional Application Ser. No. 62/338,995, filed May 19, 2016, the entire contents of each of which are hereby incorporated by reference, for all purposes, in their entirety.

This application also claims the benefit of priority to U.S. Provisional Application Ser. No. 62/899,707, filed Sep. 12, 2019, entitled "Oil-Based Wound Care Compositions and Methods," the entire contents of which are hereby incorporated by reference, for all purposes, in its entirety.

This application also claims the benefit of priority to International Application No. PCT/US2020/50596, filed Sep. 12, 2020, which claims the benefit of priority to U.S. Provisional Application Ser. No. 62/899,707, filed Sep. 12, 2019, entitled "Oil-Based Wound Care Compositions and Methods," the entire contents of each of which are hereby incorporated by reference, for all purposes, in its entirety.

FIELD

The present disclosure is broadly concerned with oil-based wound care compositions and methods for the treatment of wounds. The disclosure is also concerned with oil-based compositions for the treatment of wounds that include collagen and polihexanide biguanide (PHMB), as well as the use of such compositions as wound dressing or post-surgical dressings.

BACKGROUND

Wound care in patients and animals is a common clinical challenge faced by the healthcare and veterinary industries. Wounds may include, for example, trauma wounds, burns, ulcers, lesions, abscesses, diabetic wounds, pressure sores or ulcers, and grafts or wounds resulting from surgical procedures and operations. Wounds may result from physical injury, surgical procedures and operations, heat or chemical burns, pressure on the skin, radiation, infections, immune system deficiencies, malnourishment, as well as various medical conditions such as vascular disorders and diabetes.

Collagen is known to improve wound healing and stimulate tissue growth and is well-tolerated at the wound site. In particular, collagen is thought to aid in the migration of fibroblasts and keratinocytes to the wound site thereby improving tissue growth in the wound bed. Improved collagen wound care compositions are desirable.

DETAILED DESCRIPTION

The present disclosure provides compositions and methods for dressing and/or treating wounds in a subject. It has been unexpectedly discovered that the presently disclosed oil-based compositions comprising micronized or powdered collagen and one or more polar antimicrobial ingredients, such as polyhexamethylene biguanide (PHMB), suspended in an oil-based carrier, are especially effective in the treatment of wounds. In particular, it has been discovered that the presently disclosed compositions provide for improved penetration and absorption of collagen throughout the wound site, thereby enabling efficient delivery of collagen to the wound bed. The presently disclosed compositions may also enable delivery of collagen and PHMB through the skin graft layer and to the base of the graft thereby improving healing in skin graft or allograft patients. It has also been unexpectedly been found that presently disclosed PHMB and collagen compositions, when prepared according to the presently disclosed techniques, synergistically results in improved wound healing and lower incidence of infection as compared to separate administration of PHMB compositions and collagen compositions. Additionally, it has been found that the presently disclosed oil-based compositions are more effective in accelerating healing and preventing infection than solid substrate collagen-based wound dressings that contain PHMB or that are infused or impregnated with PHMB. In some instances, the oil-based carrier melts or otherwise liquefies once applied to the wound site due to the heat of the skin and wound, causing the release or increasing the availability of the PHMB and collagen to the wound site and aiding in the absorption and penetration of the collagen and PHMB by the wound site.

According to at least one aspect of the present disclosure, an oil-based composition for the treatment or dressing of a wound is provided. The composition may include an oil-based carrier, a polar solvent comprising one or more polar antimicrobial agents, and collagen or a collagen-based material. The polar solvent comprising one or more polar antimicrobial agents is suspended in the oil-based carrier. In at least some instances, the polar solvent comprising the one or more antimicrobial agents is dispersed in the oil-based carrier to form a stable suspension such that the solvent and polar antimicrobial agent does not separate from the oil-based carrier for at least six months. In at least some instances, the collagen or collagen-based material is suspended in the oil-based carrier and does not separate from the oil-based carrier for at least six months.

In at least some instances, the collagen or collagen-based material is in powdered form. In some cases, the collagen or collagen-based material is micronized collagen. The collagen or collagen-based material may be characterized by an average particle size of from about 5 microns to about 80 microns, or from about 20 microns to about 70 microns, or from about 5 microns to about 30 microns, or from about 10 microns to about 30 microns, or from about 15 microns to about 30 microns. In some instances, the collagen or collagen-based material is characterized by an average particle size of less than 20 microns or less than 30 microns.

The collagen or collagen-base material may be a material selected from extracellular matrix materials, micronized extracellular matrix, purified collagen, Type I collagen, Type II collagen, Type III collagen, Type X collagen, collagen fibers, collagen fibrils, micronized collagen, defibrillated collagen, coarse collagen bundles, non-crosslinked collagen, non-mineralized collage, collagen treated to control cross-linking (e.g., via chemical, thermal, photo, or radiation-induced cross-linking), collagen-glycosaminoglycan (GAG) mixtures, and any combination thereof.

The collagen or collagen-based material may comprises from about 5 wt % to about 35 wt %, or from about 5 wt % to about 25 wt %, or from about 5 wt % to about 20 wt %, or from about 5 wt % to about 15 wt %, or from about 15 wt % to about 30 wt %, of the oil-based composition.

The oil-based based carrier may be selected from animal oil, vegetable oil, natural oil, synthetic oil, hydrocarbon oils, silicone oils, and semi-synthetic derivatives thereof, and any combination thereof. The oil-based carrier may also be petrolatum, cocoa butter, jojoba oil, olive oil, soybean oil, coconut oil, beeswax, lanolin wax, carnauba wax, stearic acid, or any mixture thereof. The oil-based carrier may also be mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, C12-15 alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, *eucalyptus* leaf oil, lemon grass leaf oil, *melaleuca* leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, *cassia* Bark oil, cinnamon bark oil, *sassafras* Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combination thereof.

In some instances, the polar solvent may be water, ethanol, or a mixture of ethanol and water. In some cases, the polar solvent may further include ascetic acid. In some aspects, the one or more polar antimicrobial agents comprises a cationic biocide. The cationic biocide may be benzalkonium chloride, cetrimide, chlorhexidine, polihexanide biguanide (polihexanide, polyhexamethylene biguanide, polyhexamethylene guanide, poly(iminoimidocarbonyl-iminoimidocarbonyl-iminohexamethylene), poly (hexamethylenebiguanide), polyaminopropyl biguanide), and salts or combinations thereof. The polar solvent may further include a preservative selected from the group consisting of benzalkonium chloride, cetrimide, chlorhexidine, and any combination thereof. In some instances, the composition comprises from about 0.001% to about 0.15% by weight benzalkonium chloride (BZK). In other instances, the composition comprises from about 0.001% to about 0.01% by weight or from about 0.005% to about 0.007% by weight benzalkonium chloride (BZK).

The presently disclosed compositions may further include one or more therapeutic agents selected from the group consisting of stem cells, TGF-alpha, TGF-beta (TGFβ1, TGFβ2, TGFβ3), platelet-derived growth factor (PDGF), epidermal growth factor (EGF), fibroblast growth factor also referred to as keratinocyte growth factor (FGF1, FGF2, FGF4, FGF7), vascular endothelial growth factor (VEGF), insulin-like growth factor (IGF), connective tissue growth factor (CTGF), activin, interleukin-1 (IL1α, IL1β), TNFα, GM-CSF, a powdered antibiotic, an antifungal agent, a hemostatic agent, cytokines, and hyaluronic acid.

According to at least one aspect of the present disclosure, the presently disclosed compositions may be prepared by a process that includes: a) dissolving the one or more polar antimicrobial agents in a polar solvent to give an antimicrobial agent solution; b) heating the oil-based carrier to a temperature sufficient to cause the oil-based carrier to melt or to a temperature sufficient to provide a oil-based carrier density capable of suspending a powdered collagen or a powdered collagen-based material, resulting in a melted oil-based carrier; c) mixing a powdered collagen or a powdered collagen-based material into the melted oil-based carrier to give a suspended collagen oil-based carrier composition; d) heating the antimicrobial agent solution to a temperature higher than the temperature of the melted oil-based carrier to give a heated antimicrobial solution; e) mixing the suspended collagen oil-based carrier composition and the heated antimicrobial solution to give a melted mixture; and f) cooling the melted mixture to give the oil-based composition. In some instances, the heated antimicrobial solution has a temperature that is about 1° C. to about 5° C. higher, or about 1° C. to about 10° C. higher, or about 1° C. to about 15° C. higher, than the temperature of the suspended collagen oil-based carrier composition at the time of mixing.

In some instances, the polar antimicrobial agent is polyhexamethylene biguanide (PHMB) and the oil-based carrier is petrolatum. In such instances, the PHMB may be dissolved in a polar solvent to form a PHMB solution and the PHMB solution dispersed in the petrolatum containing collagen. In such cases, the PHMB solution may be dispersed in the petrolatum containing collagen to form a stable suspension such that the PHMB solution does not separate from the petrolatum for at least six months. Additionally, the collagen or collagen-based material remains suspended in the petrolatum for at least six months. According to at least one aspect, the petrolatum-based collagen/PHMB compositions contain no emulsifier.

The presently disclosed petrolatum-based collagen/PHMB compositions may be prepared by a process that includes: a) dissolving the PHMB in a polar solvent to give a PHMB solution; b) heating the petrolatum to a temperature sufficient to cause the petrolatum to melt to give a melted petrolatum; c) adding collagen or a collagen-based material to the melted petrolatum to give a suspended collagen melted petrolatum mixture; d) heating the PHMB solution to a temperature higher than the temperature of the melted petrolatum to give a heated PHMB solution; e) mixing the suspended collagen melted petrolatum mixture and the heated PHMB solution to give a melted mixture; and f) cooling the melted mixture to give the petrolatum-based composition collagen/PHMB composition. In some instances, the PHMB solution is heated to a temperature that is about 1° C. to about 5° C. higher than the temperature of the suspended collagen melted petrolatum mixture. According to at least one aspect of the present disclosure, the resultant petrolatum-based collagen/PHMB composition does not require an emulsifier to form a stable suspension of collagen or PHMB dispersed in the petrolatum. Further, the petrolatum-based PHMB composition prepared according to this process does not require high shear mixing to form a stable suspension of collagen and PHMB in petrolatum in the absence of an added emulsifier.

In instances in which the oil-based carrier is petrolatum, the composition may include greater than about 60% by weight petrolatum, or greater than about 70% by weight petrolatum, or greater than about 80% by weight petrolatum, or greater than about 90% by weight petrolatum. According to one aspect, the presently disclosed compositions may include from about 0.1% to about 1% by weight PHMB, or from about 0.05% to about 5% by weight PHMB, or from about 0.05% to about 3% by weight PHMB, or from about 0.2% to about 0.6% by weight PHMB, or from about 0.3% to about 0.5% by weight PHMB, or from about 0.1% to about 3.5% by weight PHMB, or from about 0.05% to about 2.5% by weight PHMB, or from about 0.5% to about 3% by weight PHMB, or from about 0.5% to about 2.5% by weight PHMB, or from about 1.5% to about 2.5% by weight PHMB.

PHMB is closely related to the polymeric biguanide polyaminopropyl biguanide (PAPB). Therefore, in at least some instances, polyaminopropyl biguanide (PAPB) may be substituted for the PHMB in the presently disclosed compositions and methods. For example, the oil-based wound care compositions may include from about 0.005% to about 5% by weight PAPB, or from about 0.01% to about 5% by weight PAPB, or from about 0.05% to about 5% by weight PAPB, or from about 0.05% to about 3% by weight PAPB, or from about 0.1% to about 1% by weight PAPB, or from about 0.2% to about 0.6% by weight PAPB, or from about 0.3% to about 0.5% by weight PAPB, or from about 0.1% to about 3.5% by weight PAPB, or from about 0.05% to about 2.5% by weight PAPB, or from about 0.5% to about 3% by weight PAPB, or from about 0.5% to about 2.5% by weight PAPB, or from about 1.5% to about 2.5% by weight PAPB.

In general, the presently disclosed compositions are topical compositions suitable for application to the wound of a subject in need thereof. In some instances, the presently disclosed compositions may take the form of an oil, or an ointment, or a cream suitable for topical administration to a wound site.

According to at least one aspect of the present disclosure, a method of treating or dressing a wound in a subject is provided. The method includes applying the presently disclosed compositions to a wound, post-surgical wound, or a post-surgical skin graft in need of dressing or treatment. The method may further include covering the composition with a wound covering selected from the group consisting of a bandage, wrap, gauze, sponge, and film, following the application of the composition to the wound or graft in need of treatment.

According to one aspect of the present disclosure, a method of treating or dressing a wound in a subject may include contacting the presently disclosed compositions to a wound covering, wherein the wound covering is a selected from the group consisting of a bandage, wrap, gauze, sponge, and film. The method may further include applying the wound covering to the wound or graft in need of treatment. Alternatively, the method may include impregnating the wound covering with the presently disclosed compositions and applying the wound covering to the wound or graft in need of treatment.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1. Formulation Example 1

An oil-based wound care composition is prepared in accordance with the present disclosure by dissolving a polar antimicrobial agent in a polar solvent to give a antimicrobial agent solution. Then an oil-based carrier is heated to a temperature sufficient to cause the oil-based carrier to melt or to a temperature sufficient to provide an oil-based carrier density capable of suspending a powdered collagen or a powdered collagen-based material, to produce a melted oil-based carrier. Next, a powdered collagen or a powdered collagen-based material is mixed into the melted oil-based carrier to give a suspended collagen oil-based carrier composition. The antimicrobial agent solution is then heated to a temperature higher than the temperature of the melted oil-based carrier to give a heated antimicrobial solution. Next, the suspended collagen oil-based carrier composition is mixed with the heated antimicrobial solution to give a melted mixture. Finally, the melted mixture is cooled to give the oil-based composition.

Example 2. Formulation Example 2

An oil-based wound care composition is prepared in accordance with the present disclosure by dissolving polyhexamethylene biguanide (PHMB) in water to give a PHMB antimicrobial agent solution. Then coconut oil is heated to 30° C., to produce a melted coconut oil-based carrier. Next, micronized collagen powder is mixed into the melted coconut oil-based carrier to give a suspended collagen coconut oil-based carrier composition. The average particle size of the micronized collagen is from about 5 microns to about 80 microns. The PHMB antimicrobial agent solution is then heated to 35° C. to give a heated PHMB antimicrobial solution. Next, the suspended collagen coconut oil-based carrier composition is mixed with the heated PHMB antimicrobial solution to give a melted mixture. Finally, the melted mixture is cooled to give the coconut oil-based composition that comprises from about 60 wt % to 90 wt % coconut oil, from about 5 wt % to about 35 wt % collagen, from about 0.05 wt % to about 5 wt % PHMB, and from about 1 wt % to about 15 wt % water.

Example 3. Formulation Example 3

An oil-based wound care composition is prepared in accordance with the present disclosure by dissolving polyhexamethylene biguanide (PHMB) and benzalkonium chloride (BZK) in water to give a PHMB/BZK antimicrobial agent solution. Then coconut oil is heated to 30° C., to produce a melted coconut oil-based carrier. Next, micronized collagen powder is mixed into the melted coconut oil-based carrier to give a suspended collagen coconut oil-based carrier composition. The average particle size of the micronized collagen is from about 5 microns to about 80 microns. The PHMB/BZK antimicrobial agent solution is then heated to 35° C. to give a heated PHMB/BZK antimicrobial solution. Next, the suspended collagen coconut oil-based carrier composition is mixed with the heated PHMB/BZK antimicrobial solution to give a melted mixture. Finally, the melted mixture is cooled to give the coconut oil-based composition that comprises from about 60 wt % to 90 wt % coconut oil, from about 5 wt % to about 35 wt % collagen, from about 0.05 wt % to about 5 wt % PHMB, from about 0.001 wt % to about 0.15 wt % BZK, and from about 1 wt % to about 15 wt % water.

Example 4. Formulation Example 4

An oil-based wound care composition is prepared in accordance with the present disclosure by dissolving chlorhexidine in water to give a chlorhexidine antimicrobial agent solution. Then coconut oil is heated to 30° C., to produce a melted coconut oil-based carrier. Next, micronized collagen powder is mixed into the melted coconut oil-based carrier to give a suspended collagen coconut oil-based carrier composition. The average particle size of the micronized collagen is from about 5 microns to about 80 microns. The chlorhexidine antimicrobial agent solution is then heated to 35° C. to give a heated chlorhexidine antimicrobial solution. Next, the suspended collagen coconut oil-based carrier composition is mixed with the heated chlorhexidine antimicrobial solution to give a melted mixture. Finally, the melted mixture is cooled to give the coconut oil-based composition that comprises from about 60 wt % to 90 wt % coconut oil, from about 5 wt % to about 35 wt % collagen, from about 0.05 wt % to about 5 wt % chlorhexidine, and from about 1 wt % to about 15 wt % water.

Example 5. Formulation Example 5

An oil-based wound care composition is prepared in accordance with the present disclosure by dissolving polyhexamethylene biguanide (PHMB) in ethanol to give a PHMB antimicrobial agent solution. Then coconut oil is heated to 30° C., to produce a melted coconut oil-based carrier. Next, micronized collagen powder is mixed into the melted coconut oil-based carrier to give a suspended collagen coconut oil-based carrier composition. The average particle size of the micronized collagen is from about 5 microns to about 80 microns. The PHMB antimicrobial agent solution is then heated to 35° C. to give a heated PHMB antimicrobial solution. Next, the suspended collagen coconut oil-based carrier composition is mixed with the heated PHMB antimicrobial solution to give a melted mixture. Finally, the melted mixture is cooled to give the coconut oil-based composition that comprises from about 60 wt % to 90 wt % coconut oil, from about 5 wt % to about 35 wt % collagen, from about 0.05 wt % to about 5 wt % PHMB, and from about 1 wt % to about 15 wt % ethanol.

Example 6. Formulation Example 6

An oil-based wound care composition is prepared in accordance with the present disclosure by dissolving polyhexamethylene biguanide (PHMB) in a mixture of 75% water and 25% ethanol to give a PHMB antimicrobial agent solution. Then coconut oil is heated to 30° C., to produce a melted coconut oil-based carrier. Next, micronized collagen powder is mixed into the melted coconut oil-based carrier to give a suspended collagen coconut oil-based carrier composition. The average particle size of the micronized collagen is from about 5 microns to about 80 microns. The PHMB antimicrobial agent solution is then heated to 35° C. to give a heated PHMB antimicrobial solution. Next, the suspended collagen coconut oil-based carrier composition is mixed with the heated PHMB antimicrobial solution to give a melted mixture. Finally, the melted mixture is cooled to give the coconut oil-based composition that comprises from about 60 wt % to 90 wt % coconut oil, from about 5 wt % to about 35 wt % collagen, from about 0.05 wt % to about 5 wt % PHMB, from about 0.75 wt % to about 11.25 wt % water, and from about 0.25 wt % to about 3.75 wt % ethanol.

Example 7. Formulation Example 7

An oil-based wound care composition is prepared in accordance with the present disclosure by dissolving polyhexamethylene biguanide (PHMB) in ascetic acid to give a PHMB antimicrobial agent solution. Then coconut oil is heated to 30° C., to produce a melted coconut oil-based carrier. Next, micronized collagen powder is mixed into the melted coconut oil-based carrier to give a suspended collagen coconut oil-based carrier composition. The average particle size of the micronized collagen is from about 5 microns to about 80 microns. The PHMB antimicrobial agent solution is then heated to 35° C. to give a heated PHMB antimicrobial solution. Next, the suspended collagen coconut oil-based carrier composition is mixed with the heated PHMB antimicrobial solution to give a melted mixture. Finally, the melted mixture is cooled to give the coconut oil-based composition that comprises from about 60 wt % to 90 wt % coconut oil, from about 5 wt % to about 35 wt % collagen, from about 0.05 wt % to about 5 wt % PHMB, and from about 1% to about 15% ascetic acid.

Example 8. Formulation Example 8

An oil-based wound care composition is prepared in accordance with the present disclosure by dissolving polyaminopropyl biguanide (PAPB) in water to give a PAPB antimicrobial agent solution. Then coconut oil is heated to 30° C., to produce a melted coconut oil-based carrier. Next, micronized collagen powder is mixed into the melted coconut oil-based carrier to give a suspended collagen coconut oil-based carrier composition. The average particle size of the micronized collagen is from about 5 microns to about 80 microns. The PAPB antimicrobial agent solution is then heated to 35° C. to give a heated PHMB antimicrobial solution. Next, the suspended collagen coconut oil-based carrier composition is mixed with the heated PAPB antimicrobial solution to give a melted mixture. Finally, the melted mixture is cooled to give the coconut oil-based composition that comprises from about 60 wt % to 90 wt % coconut oil, from about 5 wt % to about 35 wt % collagen, from about 0.05 wt % to about 5 wt % PAPB, and from about 1 wt % to about 15 wt % water.

Example 9. Formulation Example 9

An oil-based wound care composition is prepared in accordance with the present disclosure by dissolving polyhexamethylene biguanide (PHMB) in water to give a PHMB antimicrobial agent solution. Then carnauba wax is heated to 84° C., to produce a melted carnauba wax-based carrier. Next, micronized collagen powder is mixed into the melted carnauba wax-based carrier to give a suspended collagen carnauba wax-based carrier composition. The average particle size of the micronized collagen is from about 5 microns to about 80 microns. The PHMB antimicrobial agent solution is then heated to 87° C. to give a heated PHMB antimicrobial solution. Next, the suspended collagen carnauba wax-based carrier composition is mixed with the heated PHMB antimicrobial solution to give a melted mixture. Finally, the melted mixture is cooled to give the carnauba wax-based composition that comprises from about 60 wt % to 90 wt % carnauba wax, from about 5 wt % to about 35 wt % collagen, from about 0.05 wt % to about 5 wt % PHMB, and from about 1 wt % to about 15 wt % water.

Example 10. Formulation Example 10

An oil-based wound care composition is prepared in accordance with the present disclosure by dissolving polyhexamethylene biguanide (PHMB) in water to give a PHMB antimicrobial agent solution. Then beeswax is heated to 68° C., to produce a melted beeswax-based carrier. Next, micronized collagen powder is mixed into the melted beeswax-based carrier to give a suspended collagen beeswax-based carrier composition. The average particle size of the micronized collagen is from about 5 microns to about 80 microns. The PHMB antimicrobial agent solution is then heated to 72° C. to give a heated PHMB antimicrobial solution. Next, the suspended collagen beeswax-based carrier composition is mixed with the heated PHMB antimicrobial solution to give a melted mixture. Finally, the melted mixture is cooled to give the beeswax-based composition that comprises from about 60 wt % to 90 wt % beeswax, from about 5 wt % to about 35 wt % collagen, from about 0.05 wt % to about 5 wt % PHMB, and from about 1 wt % to about 15 wt % water.

Example 11. Formulation Example 11

An oil-based wound care composition is prepared in accordance with the present disclosure by dissolving polyhexamethylene biguanide (PHMB) in water to give a PHMB antimicrobial agent solution. Then petrolatum is heated to 42° C., to produce a melted petrolatum-based carrier. Next, micronized collagen powder is mixed into the melted petrolatum-based carrier to give a suspended collagen petrolatum oil-based carrier composition. The average particle size of the micronized collagen is from about 5 microns to about 80 microns. The PHMB antimicrobial agent solution is then heated to 45° C. to give a heated PHMB antimicrobial solution. Next, the suspended collagen petrolatum-based carrier composition is mixed with the heated PHMB antimicrobial solution to give a melted mixture. Finally, the melted mixture is cooled to give the petrolatum-based composition that comprises from about 60 wt % to 90 wt % petrolatum, from about 5 wt % to about 35 wt % collagen, from about 0.05 wt % to about 5 wt % PHMB, and from about 1 wt % to about 15 wt % water.

Example 12. Formulation Example 12

An oil-based wound care composition is prepared in accordance with the present disclosure by dissolving polyhexamethylene biguanide (PHMB) and benzalkonium chloride (BZK) in water to give a PHMB/BZK antimicrobial agent solution. Then petrolatum is heated to 42° C., to produce a melted petrolatum-based carrier. Next, micronized collagen powder is mixed into the melted petrolatum-based carrier to give a suspended collagen petrolatum-based carrier composition. The average particle size of the micronized collagen is from about 5 microns to about 80 microns. The PHMB/BZK antimicrobial agent solution is then heated to 45° C. to give a heated PHMB/BZK antimicrobial solution. Next, the suspended collagen petrolatum-based carrier composition is mixed with the heated PHMB/BZK antimicrobial solution to give a melted mixture. Finally, the melted mixture is cooled to give the petrolatum-based composition that comprises from about 60 wt % to 90 wt % petrolatum, from about 5 wt % to about 35 wt % collagen, from about 0.05 wt % to about 5 wt % PHMB, from about 0.001 wt % to about 0.15 wt % BZK, and from about 1 wt % to about 15 wt % water.

Example 13. Formulation Example 13

An oil-based wound care composition is prepared in accordance with the present disclosure by dissolving chlorhexidine in water to give a chlorhexidine antimicrobial agent solution. Then petrolatum is heated to 42° C., to produce a melted petrolatum-based carrier. Next, micronized collagen powder is mixed into the melted petrolatum-based carrier to give a suspended collagen petrolatum-based carrier composition. The average particle size of the micronized collagen is from about 5 microns to about 80 microns. The chlorhexidine antimicrobial agent solution is then heated to 45° C. to give a heated chlorhexidine antimicrobial solution. Next, the suspended collagen petrolatum oil-based carrier composition is mixed with the heated chlorhexidine antimicrobial solution to give a melted mixture. Finally, the melted mixture is cooled to give the petrolatum-based composition that comprises from about 60 wt % to 90 wt % petrolatum, from about 5 wt % to about 35 wt % collagen, from about 0.05 wt % to about 5 wt % chlorhexidine, and from about 1 wt % to about 15 wt % water.

Example 14. Formulation Example 14

An oil-based wound care composition is prepared in accordance with the present disclosure by dissolving polyhexamethylene biguanide (PHMB) in ethanol to give a PHMB antimicrobial agent solution. Then petrolatum is heated to 42° C., to produce a melted petrolatum-based carrier. Next, micronized collagen powder is mixed into the melted petrolatum-based carrier to give a suspended collagen petrolatum-based carrier composition. The average particle size of the micronized collagen is from about 5 microns to about 80 microns. The PHMB antimicrobial agent solution is then heated to 45° C. to give a heated PHMB antimicrobial solution. Next, the suspended collagen petrolatum-based carrier composition is mixed with the heated PHMB antimicrobial solution to give a melted mixture. Finally, the melted mixture is cooled to give the petrolatum-based composition that comprises from about 60 wt % to 90 wt % petrolatum, from about 5 wt % to about 35 wt % collagen, from about 0.05 wt % to about 5 wt % PHMB, and from about 1 wt % to about 15 wt % ethanol.

Example 15. Formulation Example 15

An oil-based wound care composition is prepared in accordance with the present disclosure by dissolving polyhexamethylene biguanide (PHMB) in a mixture of 75% water and 25% ethanol to give a PHMB antimicrobial agent solution. Then petrolatum is heated to 42° C., to produce a melted petrolatum-based carrier. Next, micronized collagen powder is mixed into the melted petrolatum-based carrier to give a suspended collagen petrolatum-based carrier composition. The average particle size of the micronized collagen is from about 5 microns to about 80 microns. The PHMB antimicrobial agent solution is then heated to 45° C. to give a heated PHMB antimicrobial solution. Next, the suspended collagen petrolatum-based carrier composition is mixed with the heated PHMB antimicrobial solution to give a melted mixture. Finally, the melted mixture is cooled to give the petrolatum-based composition that comprises from about 60 wt % to 90 wt % petrolatum, from about 5 wt % to about 35 wt % collagen, from about 0.05 wt % to about 5 wt % PHMB, from about 0.75 wt % to about 11.25 wt % water, and from about 0.25 wt % to about 3.75 wt % ethanol.

Example 16. Formulation Example 16

An oil-based wound care composition is prepared in accordance with the present disclosure by dissolving polyhexamethylene biguanide (PHMB) in ascetic acid to give a PHMB antimicrobial agent solution. Then petrolatum is heated to 42° C., to produce a melted petrolatum-based carrier. Next, micronized collagen powder is mixed into the melted petrolatum-based carrier to give a suspended collagen petrolatum-based carrier composition. The average particle size of the micronized collagen is from about 5 microns to about 80 microns. The PHMB antimicrobial agent solution is then heated to 45° C. to give a heated PHMB antimicrobial solution. Next, the suspended collagen petrolatum-based carrier composition is mixed with the heated PHMB antimicrobial solution to give a melted mixture. Finally, the melted mixture is cooled to give the petrolatum-based composition that comprises from about 60 wt % to 90 wt % petrolatum, from about 5 wt % to about 35 wt % collagen, from about 0.05 wt % to about 5 wt % PHMB, and from about 1% to about 15% ascetic acid.

Example 17. Formulation Example 17

An oil-based wound care composition is prepared in accordance with the present disclosure by dissolving polyaminopropyl biguanide (PAPB) in water to give a PAPB antimicrobial agent solution. Then petrolatum is heated to 42° C., to produce a melted petrolatum-based carrier. Next, micronized collagen powder is mixed into the melted petrolatum-based carrier to give a suspended collagen petrolatum-based carrier composition. The average particle size of the micronized collagen is from about 5 microns to about 80 microns. The PAPB antimicrobial agent solution is then heated to 45° C. to give a heated PHMB antimicrobial solution. Next, the suspended collagen petrolatum-based carrier composition is mixed with the heated PAPB antimicrobial solution to give a melted mixture. Finally, the melted mixture is cooled to give the petrolatum-based composition that comprises from about 60 wt % to 90 wt % petrolatum, from about 5 wt % to about 35 wt % collagen, from about 0.05 wt % to about 5 wt % PAPB, and from about 1 wt % to about 15 wt % water.

Example 18. Stability—3 Months

Formulation Examples 1-17 will be packaged in tubes and subjected to an accelerated stability study. Portions of Formulation Examples 1-17 will be placed sideways in a 40° C.±2° C./75%±5% relative humidity (RH) storage chamber for different intervals to yield a period of three months. The product will be assessed for physical and analytical characteristics. Formulation Examples 1-17 will exhibit no separation of components for at least 3 months when stored at 40° C.±2° C. and 75%±5% relative humidity. Additionally, the collagen will remain suspended for at least 3 months when stored at 40° C.±2° C. and 75%±5% relative humidity. Further, the antimicrobial agent will remain effective for at least 3 months when stored at 40° C.±2° C. and 75%±5% relative humidity.

Example 19. Stability—6 Months

Formulation Examples 1-17 will be packaged in tubes and subjected to an accelerated stability study. Portions of Formulation Examples 1-17 will be placed sideways in a 40° C.±2° C./75%±5% relative humidity (RH) storage chamber for different intervals to yield a period of six months. The product will be assessed for physical and analytical characteristics. Formulation Examples 1-17 will exhibit no separation of components for at least 6 months when stored at 40° C.±2° C. and 75%±5% relative humidity. Additionally, the collagen will remain suspended for at least 6 months when stored at 40° C.±2° C. and 75%±5% relative humidity. Further, the antimicrobial agent will remain effective for at least 6 months when stored at 40° C.±2° C. and 75%±5% relative humidity.

Example 20. Topical Administration of Formulation Examples 1-17 Will Improve Clinical Outcomes in Subjects Having a Wound The effect of topical administration of the oil-based wound care compositions disclosed in Formulation Examples 1-17 will be studied using a randomized, double-blind clinical study. During the clinical study, a group of human subjects will be topically administered a composition from Formulation Examples 1-17. In particular, the oil-based wound care composition will be topically applied to a wound in need of dressing or treatment in a subject. Subjects receiving treatment using the compositions of Formulation Examples 1-17 are expected to have improved standard clinical outcomes. In particular, subjects receiving treatment according to the presently disclosed methods and techniques are expected to exhibit an improvement in wound healing rate and/or a reduction in incidence of infection at the wound site.

Example 21. Topical Administration of Formulation Examples 1-17 Will Improve Clinical Outcomes in Subjects Having a Post-Surgical Wound The effect of topical administration of the oil-based wound care compositions disclosed in Formulation Examples 1-17 will be studied using a randomized, double-blind clinical study. During the clinical study, a group of human subjects will be topically administered a composition from Formulation Examples 1-17. In particular, the oil-based wound care composition will be topically applied to a post-surgical wound in need of dressing or treatment in a subject. Subjects receiving treatment using the compositions of Formulation Examples 1-17 are expected to have improved standard clinical outcomes. In particular, subjects receiving treatment according to the presently disclosed methods and techniques are expected to exhibit an improvement in wound healing rate and/or a reduction in incidence of infection at the wound site.

Example 22. Topical Administration of Formulation Examples 1-17 Will Improve Clinical Outcomes in Subjects Having a Skin Graft The effect of topical administration of the oil-based wound care compositions disclosed in Formulation Examples 1-17 will be studied using a randomized, double-blind clinical study. During the clinical study, a group of human subjects will be topically administered a composition from Formulation Examples 1-17. In particular, the oil-based wound care composition will be topically applied to a post-surgical skin graft in need of dressing or treatment in a subject. Subjects receiving treatment using the compositions of Formulation Examples 1-17 are expected to have improved standard clinical outcomes. In particular, subjects receiving treatment according to the presently disclosed methods and techniques are expected to exhibit an improvement in wound healing rate and/or a reduction in incidence of infection at the skin graft site.

Example 23. Topical Administration of Formulation Examples 1-17 Will Improve Clinical Outcomes in Subjects Receiving a Wound Covering The effect of topical administration of a wound covering comprising the oil-based wound care compositions disclosed in Formulation Examples 1-17 will be studied using a randomized, double-blind clinical study. During the clinical study, a group of human subjects will be topically administered a wound covering comprising the composition from Formulation Examples 1-17. In particular, the oil-based wound care compositions according to Formulation Examples 1-17 will be applied to a wound covering such as a bandage, wrap, gauze, sponge, or film. In some instances, the wound covering may be impregnated or saturated with the oil-based wound care compositions according to Formulation Examples 1-17. In other instances, the wound covering may be just contacted with the oil-based wound care compositions disclosed in Formulation Examples 1-17. The treated wound covering will be topically applied to a wound or post-surgical skin graft in need of dressing or treatment in a subject. Subjects receiving treatment using the wound coverings treated with the oil-based wound care compositions of Formulation Examples 1-17 are expected to have improved standard clinical outcomes. In particular, subjects receiving treatment according to the presently disclosed methods and techniques are expected to exhibit an improvement in wound healing rate and/or a reduction in incidence of infection at the wound or skin graft site.

Example 24. Methods of Use

In one embodiment, the compositions may be applied topically to a subject in need to deliver active ingredients such as one or more cationic biocides or collagen to the wound site. The subject is preferably human but the composition may also be useful in animals, for example domestic animals, livestock, or other types of animals. Application to the skin includes application to a wound site at any stage of healing. For example, the composition may be applied to the site of an abrasion, abscess, an arterial ulcer, the site of a burn, the site of debridement, a diabetic ulcer, dry or clotted blood, epithelial tissue, gangrene, a lesion, maceration, necrosis, rash, surgical incisions, and to wounds generally.

Alternatively, the compositions described herein may be used intraoperatively, or left internally at skin closure following surgery. The composition may also be used postoperatively as a topical dressing to deliver an active ingredient on a clean, closed site. The compositions described herein may also be useful in negative pressure wound therapy, hyperbaric oxygen therapy, and as a dressing for biologic skin substitutes. In negative pressure applications, the composition may be used to moisten sponges and dressings commonly used in negative pressure apparatuses. The composition may also be used as a personal lubricant or a lubricant for diagnostic uses. This list is intended to be exemplary and non-limiting.

In still another aspect, the invention encompasses a method of treating or preventing a skin condition using the composition described herein. The composition described herein may be applied topically to a subject in need. Specifically, the composition described herein may be applied topically to the skin of a subject in need. Subjects in need may be those with a skin condition. Subjects in need may also be subjects at risk for a skin condition. Non-limiting examples of skin conditions include acne, scarring, age-spots, dermatitis (contact dermatitis, photodermatitis, seborrheic dermatitis, nummular dermatitis, stasis dermatitis, dermatitis herpetiformis, atopic dermatitis, allergic dermatitis), cold sores, skin discoloration, eczema, rosacea, psoriasis, warts, blisters, chafing, sunburn, rash, hives wrinkling, sagging, photodamaged skin, sensitive skin, dry skin, rough skin, flaky skin, red skin, irritated skin, and itchy skin. This list is intended to be exemplary and non-limiting.

The amount of composition applied in the methods described herein can and will vary depending on the condition being treated and the severity of that condition. Generally, the amount used is sufficient to cover the affected skin area with a thin layer of the composition. The composition is applied directly to the skin. In some embodiments, the composition is spread so that it forms a thin layer over the treatment area. In other embodiments, the composition is spread by a melting action that occurs as the warmth of the patient's skin melts the petrolatum. The composition may be covered with a bandage after application. The composition may also be coated on or impregnated in a dressing, such as, for example, a bandage.

The composition when applied to the skin is non-irritant and non-cytotoxic. These properties allow the composition to be used on sensitive areas such as wounds that have recently been debrided. These characteristics also allow for delivery of the active ingredient over a long period, such as for example 2 weeks, 4 weeks, 6 weeks, 8 weeks, or longer without irritation to the treated area. It will be recognized however, that the compositions may be used for shorter periods of time if necessary.

The compositions are also capable of extended release of the active ingredient to the area of application. "Extended release" as used herein means that the compositions release active ingredients to the application site over a period of time extending past twelve hours. The time over which the extended release is provided is variable depending on the amount of the composition that is applied and on the heat of the wound, but in general, the release of active ingredients is extended beyond the initial application and active ingredients have been shown to be released for up to 1 week. This extended release allows the composition to be applied less frequently and improves patient compliance with the treatment.

The compositions of the invention also offer kinetic release when applied to the skin. Kinetic release means that the active ingredients are released to the treatment area more rapidly when the treatment area is hotter. Kinetic release can be particularly useful in treatment of infections with an antimicrobial active ingredient. Because more serious infections are hotter than less serious infections, kinetic release provides more active ingredients rapidly to the worst infections, thereby facilitating their treatment.

Example 25. Formulation Example 18

Formulation Example 18 was prepared by adding 2540.3 pounds of white petrolatum to a tank that has been cleaned and sterilized in accordance with SOP protocol. In the tank was used to heat the petrolatum to 110° C.-113° F. to melt the petrolatum. In a separate clean and sanitized container 133.70 pounds of water and the desired amount of BZK and PHMB were added and heated to 122° F. When both phases are at temperature, the solution phase was slowly added to the petrolatum with mixing. The heat was decreased slowly to 96-104° F. The product was tested for quality control and transferred to polypropylene drums. The resulting composition was shiny and white to slightly yellow in appearance. Specific gravity at 25° C. matches specification when it is from 0.830-0.910. Viscosity at @ 25° C. TF @ 10 rpm matches specification when it is from about 225,000-300,000 cps. The final formulation contained the following ingredients by weight percent: 95% petrolatum; 0.13% BZK, 0.2% PHMB, and 4.67% water.

Example 26. Skin Sensitization Evaluation

A study was conducted on the formulation prepared in Example 25, referred to herein as "Formulation Example 18" to assess skin sensitization. Patches comprising Formulation 18 were affixed directly to the skin of 53 human study participants representing an age range from 18-63 and five skin types. Table 1 presents the participant demographics. Patches remained in place for 48 hours after the first application. Participants were instructed not to remove the patches prior to their 48 hour scheduled visit. Thereafter, the subjects were instructed to remove patches for 24 hours. This procedure was repeated until a series of nine consecutive, 24 hour exposures had been made three times per week for three consecutive weeks. Test sites were evaluated by trained personnel. Following a 10-14 day rest period, a retest/challenge dose was applied once to a previously unexposed test site. Test sites were evaluated by trained personnel 48 and 96 hours after application. The sites were scored based on the International Contact Dermatitis Research Group scoring scale (Rietschel, Fowler, Ed., Fisher's Contact Dermatitis (fourth ed.). Baltimore, Williams &Wilkins, 1995) as presented in Table 2.

TABLE 1

Participant Demographics.

| | |
|---|---|
| Number of subjects enrolled | 53 |
| Number of subjects completing study | 53 |

TABLE 1-continued

Participant Demographics.

| | |
|---|---|
| Age Range | 18-63 |
| Sex | Male 13 |
| | Female 40 |
| Fitzpatrick Skin Type* | |
| 1 - always burn, does not tan | 0 |
| 2 - burn easily, tan slightly | 4 |
| 3 - burn moderately, tan progressively | 47 |
| 4 - burn a little, always tan | 2 |
| 5 - rarely burn, tan intensely | 0 |
| 6 - never burn, tan very intensely | 0 |

*Agaghe P, Hubert P. Measuring the skin. (p. 473, table 48.1) Springer-Verlag Berlin Heidelberg, 2004.

TABLE 2

Scoring Scale.

| | |
|---|---|
| 0 | No reaction (negative) |
| 1 | Erythema throughout at least ¾ of patch area |
| 2 | Erythema and induration throughout at least ¾ of patch area |
| 3 | Erythema, induration and vesicles |
| 4 | Erythema, induration and bullae |
| D | Site discontinued |
| Dc | Subject discontinued |

No adverse reactions of any kind were reported during the course of study. Accordingly, Formulation Example 18 gives no identifiable signs or symptoms of primary irritation or sensitization (contact allergy).

Example 27. Antimicrobial Efficiency Testing

Antimicrobial efficacy testing was conducted according to USP 51. Five microbes were tested. Each organism was inoculated at an inoculum level of $1 \times 10^6$ colony forming units (CFU) per gram for bacteria or $1 \times 10^5$ CFU per gram for yeast and mold. The inoculated samples were then stored at 20-25° C. for 28 days. The population of each microorganism was determined by plate counting at Day 2, 7, 14, 21, and 28. The plate counts were performed at a 1:10 initial dilution using Modified Letheen Broth as the diluent and plated onto Tryptic Soy and Sabouraud Dextrose agar.

A single application of Formulation Example 18 gave 100% elimination from day 2 to day 28 for all microbes tested (Table 3). Given the 100% elimination, there was a 4 log reduction in the yeast/mold species and a 5 log reduction in the bacterial species (Table 4). Table 5 is a positive control indicating that the method used recovers 80-100% of the microbe in the absence of Formulation Example 18. Accordingly, the microbes present in the test sample were eliminated under the tested conditions. The results illustrate the broad spectrum of activity for Formulation Example 18.

TABLE 3

Preservative Testing.

| | Colony Forming Units/gram | | | | | |
|---|---|---|---|---|---|---|
| Organism | Inoculum/g | Day 2 | Day 7 | Day 14 | Day 21 | Day 28 |
| Staphylococcus aureus (bacteria) ATCC#6538) | $1 \times 10^6$ | <10 | <10 | <10 | <10 | <10 |
| Pseudomonas aeruginosa (bacteria) (ATCC#9027) | $1 \times 10^6$ | <10 | <10 | <10 | <10 | <10 |
| Escherichia coli (bacteria) (ATCC#8739) | $1 \times 10^6$ | <10 | <10 | <10 | <10 | <10 |

TABLE 3-continued

Preservative Testing.

| | Colony Forming Units/gram | | | | |
|---|---|---|---|---|---|
| Organism | Inoculum/g | Day 2 | Day 7 | Day 14 | Day 21 | Day 28 |
| *Candida albicans* (yeast) (ATCC#10231) | 1 × 10⁵ | <10 | <10 | <10 | <10 | <10 |
| *Aspergillus niger* (mold) (ATCC#16404) | 1 × 10⁵ | <10 | <10 | <10 | <10 | <10 |

TABLE 4

Log Reduction Calculation from Initial Inoculum.

| | 14 days | 28 days |
|---|---|---|
| *Aspergillus niger* | 4.00 | 4.00 |
| *Candida albicans* | 4.00 | 4.00 |
| *Pseudomonas aeruginosa* | 5.00 | 5.00 |
| *Escherichia coli* | 5.00 | 5.00 |
| *Staphylococcus aureus* | 5.00 | 5.00 |

TABLE 5

Preservative Testing Validation.

| Organism | Inoculum | Dilution | Microbial Recovery | Diluent | Percent Recovery |
|---|---|---|---|---|---|
| *Staphylococcus aureus* | 76 cfu/plate | 1:10 | 69 cfu/plate | LB | 87% |
| *Pseudomonas aeruginosa* | 83 cfu/plate | 1:10 | 81 cfu/plate | LB | 97% |
| *Escherichia coli* | 68 cfu/plate | 1:10 | 58 cfu/plate | LB | 85% |
| *Candida albicans* | 63 cfu/plate | 1:10 | 50 cfu/plate | LB | 79% |
| *Aspergillus niger* | 60 cfu/plate | 1:10 | 60 cfu/plate | LB | 100% |

CFU = colony forming units;
LB = Letheen Broth;
Diluent = Letheen Broth;
Dilution: 1:10

Example 28: Cytotoxicity Evaluation

The study was conducted to assess the biological reactivity of mammalian cells (grown in culture) to the agar-diffusible elements of Formulation Example 18.

The samples to be evaluated for cytotoxicity include test product comprising Formulation Example 18, Amber latex tubing as a positive control, and HDPE sheet stock as a negative control. The samples were sized to have no less than 100 mm² of contact surface and provide coverage of approximately 10% of the test dish. The dimensions of the test product comprising Formulation Example 18 were 1.1× 1.1-1.2 cm; the dimensions of the positive control were 1.0×2.55-2.7 cm; and the dimensions of the negative control were 1.15×1.0-1.2 cm. The manipulation of the samples was performed aseptically.

Prior to exposure to the samples, the L929 Mouse Fibroblast cells were subcultured in Minimum Essential Medium (MEM) with 10% Fetal Bovine Serum (FBS) to achieve a confluency of approximately 80±10% at the time of exposure. The cells were examined for normal morphology and the absence of contamination. Once the cells met the acceptance criteria for use, individual dishes were numbered in triplicate to represent the controls and the test product comprising Formulation Example 18.

On the day of testing, the subculture media was carefully removed from each test dish and replaced with a 2 mL aliquot of the 1:1 overlay medium (in equal parts of 2× Minimum Essential Medium (with 2% Fetal Bovine Serum) and Agar Noble). After allowing the overlay medium to solidify, a single test product comprising Formulation 18 or control sample was placed in the center of each dish (in contact with the agar surface). Triplicate cultures were prepared for each test product comprising Formulation 18 and positive and negative controls (one sample per dish). When the test product comprising Formulation 18 or positive/negative control has only one face designated for patient-contact, that "side" of the sample was directed toward the agar. The test dishes, along with 3 dishes with overlay medium only (Monolayer Negative Controls), were then placed in the 37° C./5% $CO_2$ incubator to initiate the exposure interval.

The dishes were incubated for 24 hours and then microscopically examined for an indication of cellular response. A preliminary microscopic examination of the cells was made prior to staining and before the control and test product comprising Formulation 18 were removed from the agar layer. The cells were then stained with a fresh working Neutral Red Solution to facilitate response grading. The test product comprising Formulation Example 18 and control samples were removed from the dishes at this time. The stained cells were then fixed by the addition of buffered formalin. Following fixation, the agar overall was removed from each dish. Following staining, the cellular responses were then evaluated microscopically and macroscopically (by examining the dishes against a white surface) and the results were recorded.

For the control samples to be deemed valid, the negative controls may be no greater than Grade 0 and the positive control may be no less than Grade 3. For the test product comprising Formulation 18, a Grade of 0, 1 (slight) or 2 (mild) indicates the test product comprising Formulation Example 18 "meets" the assay acceptance criteria and a Grade of 3 (moderate) or 4 (severe) indicates the test product comprising Formulation Example 18 does not meet the assay acceptance criteria. Table 6 depicts the Grading guidelines.

TABLE 6

Grading Guidelines.

| Grade(1) | Reactivity | Description of the Reactivity Zone(2) |
|---|---|---|
| 0 | None | No detectable zone around or under specimen |
| 1 | Slight | Some malformed or degenerated cells under specimen(3) |
| 2 | Mild | Zone limited to area under specimen |
| 3 | Moderate | Zone extends 0.45 to 1.0 cm beyond specimen |
| 4 | Severe | Zone extends greater than 1.0 cm beyond specimen |

(1)The use of the above Grading Table is contingent on the test article meeting the minimum surface area requirements of ≥100 mm². Should samples of smaller dimensions be tested, the reactivity (if any) would be expected to be less and the grading would need to be justified.
(2)The extent of the Reactivity Zone is the maximum measured distance from the edge of the specimen to the margin of monolayer where degenerated cells are no longer observed. Where described as "under specimen", this maximum measured distance is limited to <0.45 cm beyond the specimen.
(3)To be interpreted as "slight" reactivity, no more than 50% of the cells under the specimen may exhibit reactivity as rounding and/or lysis.

Table 7 depicts the results of the study. The assay controls met the acceptance criteria for a valid assay. All negative controls responses were no greater than Grade 0 and the positive control response were not less than Grade 3. The responses observed for the test product comprising Formulation Example 18 were interpreted according to the current USP guidelines. The Grade response from the test product comprising Formulation Example 18 is considered to be "non-cytotoxic" (i.e. meets ISO test acceptance requirements of no more than Grade 2 reactivity). Accordingly, Formulation Example 18 does not damage mammalian cells.

TABLE 7

Study Results.

| | | Macroscopic Reading (Zone Dimensions) | Microscopic Reading (% Rounded/Lysed) | Grade |
|---|---|---|---|---|
| Monolayer Negative Control | 1 | No detectable zone | 0%/0% | 0 |
| | 2 | No detectable zone | 0%/0% | 0 |
| | 3 | No detectable zone | 0%/0% | 0 |
| Material Positive Control | 1 | Clear Zone 3.2 × 3.2; Greatest distance from specimen 1.5 cm | 100%/100% | 4 |
| | 2 | Clear Zone 3.2 × 3.2; Greatest distance from specimen 1.5 cm | 100%/100% | 4 |
| | 3 | Clear Zone 3.2 × 3.2; Greatest distance from specimen 1.5 cm | 100%/100% | 4 |
| Material Negative Control | 1 | No detectable zone | 0%/0% | 0 |
| | 2 | No detectable zone | 0%/0% | 0 |
| | 3 | No detectable zone | 0%/0% | 0 |
| Test Product Comprising Formulation 1 | 1 | Entire dish lightly stained ~5% rounded directly under sample | 1.5%/1.5% | 1 |
| | 2 | Entire dish lightly stained ~5% rounded directly under sample | 1.5%/1.5% | 1 |
| | 3 | Entire dish lightly stained ~5% rounded directly under sample | 1.5%/1.5% | 1 |

Example 29: Rabbit Skin Irritation

The study was conducted to assess the irritating potential of Formulation Example 18 to produce dermal irritation.

Within 24 hours to 4 hours before test application, the backs of female albino New Zealand White rabbits were clipped free of hair, exposing 2 test and 2 control areas on each side of the spine with a size of approximately 15 cm×15 cm. The two test sites are located on the left cranial section and the right caudal section of the dorsal region. The two control sites are located on the left caudal and right cranial section of the dorsal region. FIG. 2 depicts the arrangement of test and control sites. The exposed skin is wiped with alcohol and dried. Rabbits of acceptable skin quality were selected and used for testing.

A 25×25 mm gauze patch saturated with 0.5 mL (liquid) or 0.5 g (powder) of Formulation 18 is applied to the clipped test sites. A 25×25 mm gauze patch saturated with 0.5 mL of 0.9% NaCl is used for the control and applied to the clipped control sites. The patches are secured using hypoallergenic, waterproof, surgical tape over the test and control sites. The animal's trunk is securely wrapped so as to maintain the position of the patches. Patches are left applied for a minimum of four hours.

After patch removal, the test and control sites were then scored for erythema and edema at 1, 24, 48 and 72 hours after patch removal. Only the 24, 48, and 72 hour observations were scored and used for calculations. The criteria for scoring is presented in Table 8. If no response was expected, testing was conducted using three animals per test article. If irritation was anticipated, one animal was tested initially. If the first animal received a score of 2 or less for either erythema or edema, 2 additional rabbits were used to conclude the test.

TABLE 8

Scoring Criteria for Test Reactions.

| Reaction | Description | Score |
|---|---|---|
| Erythema (ER) | No erythema | 0 |
| | Very slight (barely perceptible) | 1 |
| | Well defined | 2 |
| | Moderate | 3 |
| | Severe (beet-redness) to eschar formation preventing grading of erythema | 4 |
| Edema (ED) | No edema | 0 |
| | Very slight (barely perceptible) | 1 |
| | Well-defined edema (edges of area well-defined by definite raising | 2 |
| | Moderate (edges raised ~1 mm) | 3 |
| | Severe (raised more than 1 mm and extending beyond exposure area) | 4 |

For each animal and each extract, when applicable, the scores for the test article comprising Formulation Example 18 for erythema and edema at each time were added. This total was divided by the total number of observations. The same was done for the control sites. The control result was subtracted from the test results to give the irritation index for each animal. These scores for each animal were added and divided by the total number of animals to give the Primary Irritation Index. The Primary Irritation Index is depicted in Table 9. For any response, the Maximum Irritation Response, the time of onset of the response and the time of maximum response was recorded.

TABLE 9

Primary Irritation Index

| Primary Irritation Index | Response Category |
|---|---|
| 0-0.4 | Negligible |
| 0.5-1.9 | Slight |
| 2-4.9 | Moderate |
| 5-8 | Severe |

The results indicated that the skin reactions for both the test article comprising Formulation 18 and control samples were not significant. That data is presented in Table 10 below. Accordingly, the Formulation Example 18 is non-irritating.

TABLE 10

Direct Application of Test Article.

|  | Formulation 1 | Control |
|---|---|---|
| Rabbit No. 14384 | ER + ED = Total<br>0 0 0<br>Test Total − Control Total = 0<br>Total Score Average = 0 | ER + ED = Total<br>0 0 0 |
| Rabbit No. 14387 | ER + ED = Total<br>0 0 0<br>Test Total − Control Total = 0<br>Total Score Average = 0 | ER + ED = Total<br>0 0 0 |
| Rabbit No. 14394 | ER + ED = Total<br>0 0 0<br>Test Total − Control Total = 0<br>Total Score Average = 0 | ER + ED = Total<br>0 0 0 |
| Total Average (0) = 0 Primary Irritation Index<br>No. of Animals (3) | | |

To positively validate the test, 10% sodium dodecyl sulfate (SDS), which is a known dermal irritant, in petroleum jelly was applied to a 2.5 cm×2.5 cm gauze patch. As a negative control, 0.5 mL of 0.9% NaCl was applied to a 2.5 cm×2.5 cm gauze patch. A Primary Irritation Index in the moderate to severe range is considered a positive result. The test system and methods utilized were the same as described above. Table 11 presents the results validating the study.

TABLE 11

Primary Skin Positive Validation Test.

|  | 10% SDS | Control |
|---|---|---|
| Rabbit No. 14279 | ER + ED = Total<br>18 14 32<br>Test Total − Control Total = 32<br>Total Score Average = 5.3 | ER + ED = Total<br>0 0 0 |
| Rabbit No. 14280 | ER + ED = Total<br>21 19 40<br>Test Total − Control Total = 40<br>Total Score Average = 6.6 | ER + ED = Total<br>0 0 0 |
| Rabbit No. 14281 | ER + ED = Total<br>23 21 44<br>Test Total − Control Total = 44<br>Total Score Average = 7.3 | ER + ED = Total<br>0 0 0 |
| Total Average (19.3) = 6.4 Primary Irritation Index<br>No. of Animals (3) | | |

Example 30. Suspension Time-Kill Procedure for MRSA, *T. rubrum*, and *Staphylococcus epidermidis*

A study was conducted to evaluate the changes in the population of MRSA in an antimicrobial liquid suspension comprising Formulation Example 18. Methicillin-resistant *Staphylococcus aureus* (MRSA) is a Gram-positive, cocci shaped, aerobe which is resistant to the penicillin-derivative antibiotic methicillin. MRSA can cause troublesome infections, and their rapid reproduction and resistance to antibiotics makes them more difficult to treat. MRSA bacteria are resistant to drying and can therefore survive on surfaces and fabrics for an extended period of time and therefore makes this bacteria an excellent representative for antimicrobial efficacy testing on surfaces.

To conduct the study, MRSA was prepared in liquid culture medium (Letheen Broth). The suspension of MRSA was standardized by dilution to $10^6$ in a buffered saline solution. Formulation 18 and control substance (PBS) were dispensed in identical volumes to sterile vessels. Independently, Formulation 18 and control substance were each inoculated with MRSA, then mixed and incubated. Control substances were immediately harvested and represented the concentration present at the start at the test (i.e. time zero). At the conclusion of contact time, a volume of the liquid test product was harvested and chemically neutralized. Dilutions of the neutralized test solution were assayed using appropriate growth media to determine the surviving MRSA at the respective contact times. Reductions in MRSA were calculated by comparing initial microbial concentrations to final microbial concentrations. Table 12 and FIG. 3 present the results of the study.

TABLE 12

Results of Suspension Time-Kill Test for MRSA (33592)

| Test substance | Contact time | Replicate | Replicate CFU/ml* | Average CFU/ml | Percent Reduction vs. Control at Time Zero | Log$_{10}$ Reduction vs. Control at Time Zero |
|---|---|---|---|---|---|---|
| PBS | Time Zero | 1 | 1.75E+06 | 1.48E+06 | N/A | |
|  |  | 2 | 1.20E+06 |  |  |  |
| Formulation 18 | 30 seconds | 1 | 1.00E+01 | <1.00E+01 | >99.9993% | >5.17 |
|  |  | 2 | <1.00E+01 |  |  |  |
|  | 2 minutes | 1 | 1.00E+01 | <1.00E+01 | >99.9993% | >5.17 |
|  |  | 2 | <1.00E+01 |  |  |  |

*The limit of detection for the assay is 1.00E+01 CFU/ml. Values below the limit of detection are notes as <1.00E+01 in the table.

The same study was conducted with *Trichophyton rubrum*. *T. rubrum* is a fungus which belongs to the dermatophyte group. Dermatophytes commonly cause skin disease in animals and humans. *T. rubrum* is anthropophilic, meaning it preferentially infects humans over animals. This parasite is the most common cause of fungal infection of the fingernail and Athlete's foot, this specific strain was isolated from a human toenail. In the laboratory, visible colonies can be observed after approximately 4-5 days and are fluffy and white in appearance. *T. rubrum* is a popular test microorganism for fungicidal testing, especially for products intended for use in environments where skin infections can occurs and spread rapidly such as locker rooms and schools.

To conduct the study, *T. rubrum* was prepared on agar (potato dextrose agar). The *T. rubrum* was resuspended and inoculated at a dilution of ~$10^6$ into vessels containing Formulation 18 and control substance (PBS). Control substances were immediately harvested and represented the concentration present at the start at the test (i.e. time zero). At the conclusion of contact time (2 or 10 minutes), a volume of the liquid test product was harvested and chemically neutralized. Dilutions of the neutralized test solution were assayed using appropriate growth media to determine the surviving *T. rubrum* at the respective contact times. Reductions in *T. rubrum* were calculated by comparing initial microbial concentrations to final microbial concentrations. Table 13 and FIG. 4 present the results of the study.

TABLE 13

Results of Suspension Time-Kill Test for *T. rubrum* (MYA-4438)

| Test substance | Contact time | Replicate | Replicate CFU/ml* | Average CFU/ml | Percent Reduction vs. Control at Time Zero | Log$_{10}$ Reduction vs. Control at Time Zero |
|---|---|---|---|---|---|---|
| PBS | Time Zero | 1 | 2.55E+05 | 3.15E+05 | N/A | |
| | | 2 | 3.75E+05 | | | |
| Formulation 18 | 2 minutes | 1 | 3.50E+03 | 2.18E+03 | 99.31% | 2.16 |
| | | 2 | 8.50E+02 | | | |
| | 10 minutes | 1 | <5.00E+01 | <5.00E+01 | >99.98% | >3.80 |
| | | 2 | 5.00E+01 | | | |

*The limit of detection for the assay is 5.00E+01 CFU/ml. Values below the limit of detection are notes as <5.00E+01 in the table.

The same study was conducted with *Staphylococcus epidermidis*. Gram-positive organisms currently account for 50-60% of nosocomial bacteremic events. *Staphylococcus epidermidis* is the most common gram-positive organism isolated from blood (30% of isolates) and accounts for the majority of infections that are associated with intravascular catheters, as it is capable of forming antibiotic resistant biofilms on plastic surfaces.

In an effort to further explore the preventative benefits of Formulation Example 18 in preventing catheter related and hospital acquired infections, a suspension time kill assay as described above was initiated on this often under-discussed organism. A nearly 7 log kill over 24 hours was observed, which represents a typical change interval for intravenous catheter dressings (Table 14).

TABLE 14

Results of Suspension Time-Kill Test for *S. epidermidis* (ATCC 12228)

| Test substance | Contact time | Replicate CFU/ml* | Percent Reduction vs. Control at Time Zero | Log$_{10}$ Reduction vs. Control at Time Zero |
|---|---|---|---|---|
| PBS | Time Zero | 4.80E+06 | N/A | |
| Formulation 1 | 24 Hours | <1.00E+00 | >99.99998% | >6.68 |

The limit of detection is 1.00E+00 and is represented as <1.00E+00.

Example 31. The Use of Formulation Example 18 in a Slow Healing Wound Complicated by Patient Non-Compliance: Case Report A 56-year-old black male presented to clinic with the chief complaint of venous ulcers of right dorsal and plantar surfaces of foot and 2nd and 3rd toes. He had a prior medical history significant for chronic lymphedema, DM, HTN, Hyperlipidemia, CVA with residual hemiparesis of right side, wheelchair bound, tobacco dependence, seizure disorder, depression and asthma. He had been treated in the past with butadiene gauze wraps and iodasorb with kling, ace, and coban wraps with little improvement. Wound care was delivered twice weekly.

The patient received Clindamycin 300 TID×7 days due to the markedly minimal improvement of wound status over the first 7 weeks of treatment. Minimal improvement was noted after the antibiotic course.

Formulation Example 18 was utilized for the first time. A thin layer was applied to affected limb and ulcerations. The limb was dressed with gauze and coban in a compression wrap with weekly dressing changes to follow in this manner. Twenty-one days later significant improvement in wound appearance was observed and the wound on dorsal surface of the right foot had resolved completely. By four weeks, the entire dorsal surface was resolved and wounds were limited to plantar surface of the right 2nd and 3rd toes. By two months, wounds on plantar surfaces of the right foot were very defined and without any maceration. By three months, wounds had become essentially dry eschars with all tissues fully epithelialized.

In summary, all previous attempts to treat the patient's extensive wounds had failed but the introduction of Formulation 18 to the treatment marked a significant turning point in his care. Even in the face of extensive non-compliance and extended dressing change intervals, Formulation 18 remained in contact with the wound and continued to manage the environment.

Example 32. Use of Formulation Example 18 in Patient with History of Delayed Healing: Case Report A 76-year-old white female presented to clinic 24 hours after sustaining a 1.0×5.0×0.1 mm laceration to her right shin. She relates that she was standing near a wood pile when some wood fell and cut her. Radiographs were negative for fracture and ultrasound found no evidence of retained foreign body. The wound did not probe to bone. Her tetanus status was brought up to date. The wound was cleaned with sterile saline, edges re-approximated, and closed with retaining sutures and simple closure sutures in local ER.

Patient's medical history was significant for diabetes mellitus type 2 insulin dependent, CKD-4, ASCVD, and CABG-4 vessel. Notably, she relates a history of poor and delayed wound healing from graph site of right lower limb which took over 3 months to heal. She also suffers from peripheral neuropathy HTN, hyperlipidemia, obesity, and PVD/PAD.

Patient was seen in clinic and expressed concerns due to her history of delayed healing. Formulation 18 was applied with a standard dry, sterile dressing. Patient was instructed to return weekly for dressing changes.

The simple sutures were removed 2 weeks later. The wound showed no signs of dehiscence or infection. Edges were well approximated and surrounding tissue was appropriate to temperature and color. Formulation 18 continued to be used exclusively.

Retaining sutures were removed a week later. The wound was showing progressing epithelialization and had significantly decreased in size. The wound was dressed with Band-Aid and Formulation 18 for home use until completely healed.

By week 4, the patient was healed. There were no issues with wound healing or closure in a patient who had previously taken 12 weeks to heal from a saphenous graph harvest site. No revascularization had been done nor had any other health factor changed since the graft. This indicates that the use of Formulation 18 played an integral role in the closure of this wound.

The only factor that was changed in the patient's wound care for this laceration was the introduction of topical Formulation 18. With use of this product, the patient showed no signs of delayed healing. Her wound granulated and epithelialized as would be expected of a person without multiple systemic diseases. Formulation 18 appeared to have facilitated non-delayed healing while keeping the wound environment moist without macerating. Additionally, Formulation 18 stayed in contact with the wound and effective for a week without requiring dressing change, which is a benefit for patients with limited resources and transportation difficulties.

Example 33. Postoperative Treatment *Streptococcus* B Perianal Abscess with Formulation Example 18: Case Report A 51-year-old woman was admitted for the management of a perianal abscess. The patient had a history of a prior perianal abscess 6 months previously and an iodine allergy. The prior abscess had been treated via bedside I&D and oral antibiotics. With the recurrence of infection, concern for the presence of an anal fistula arose and the patient was admitted under SIRS criteria for evaluation and intervention.

Parenteral antibiotics were initiated, she was taken to the operating room for definitive treatment and placed under MAC anesthesia. An I&D was performed and exploration of the perianal space revealed a transsphincteric fistula as the source of the infection. A seton was initially placed to delineate the fistula. The fistula was subsequently repaired after the abscess was drained and washed out. Post-operatively a 3.3 cm deep soft tissue deficit remained.

In light of the patient's iodine allergy, the wound could not be treated with the standard betadine treated packing strips. Instead, the wound was packed with plain packing strips treated with Formulation 18, gauze, and sealed with Tegaderm. The patient was discharged on oral antibiotics with instructions for daily dressing changes to be performed.

Daily packing changes with the Formulation 18-treated packing strips were performed. By day 10 the soft tissue defect had fully granulated and packing was discontinued. The wound was subsequently dressed with a thin layer of Formulation 18 applied to the peri-wound area, with gauze and Tegaderm to seal the peripheral edges. By day 17 wound closure had been achieved.

The rate of granulation was markedly improved with the use of Formulation 18 when compared with the rates of healing with betadine packing strips. Typical rates with betadine strips run in the 4-6-week range. The difference in the rate of granulation is attributed to the difference in cytotoxic properties of the two products. Betadine, while being bactericidal, is also cytotoxic to fibroblasts which delays healing. Formulation 18 combines bactericidal properties with non-cytotoxicity to allow a more ideal environment for healing.

This case highlights the importance using of a non-cytotoxic, anti-microbial packing in the treatment of post-operative wounds. Ultimately, shorter duration of healing reduces the likelihood of opportunistic post-op infection and the use of a topical anti-microbial as an adjunctive treatment in conjunction with oral antibiotics provides a more ideal setting for healing to take place.

Example 34. The Use of Formulation 18 in the Treatment of Severe Abrasions: Case Report A 22-year old healthy male with no comorbidities was admitted to the emergency room with 2nd degree abrasions secondary to a locker room injury. Patient's tetanus status was addressed and wounds were cleaned and dressed with triple-antibiotic ointment, sterile gauze, and impregnated silver mesh. Patient and his parents were instructed to continue this dressing course BID upon release.

Five days post-hospitalization saw no visible reduction in wound state. Patient expressed distress over necrosis formation at the site and a 5/10 pain level. A trial of Formulation 18 with sterile gauze and paper tape was initiated at this point.

The wound was flushed with sterile saline, blotted dry, and a thin layer of Formulation 18 was applied topically to the wound bed and surrounding tissue. Wound dressing consisted of sterile gauze, kerlix, and paper tape. Patient was instructed to continue dressing changes BID, in the manner described.

By day 3 of treatment with Formulation 18, the wound had visibly improved. The eschar had autolytically debrided and the wound profile showed granular bases with well demarcated borders and the formation of skin islands. Patient reported a reduction of pain to 2/10.

After 10 days of dressing changes utilizing Formulation 18, the epithelial layer of skin had regenerated peripherally with mild central eschars at the central aspect of the wound bases. Pain was eliminated. Patient was able to resume normal activity at 10 days.

A rapid rate of healing, pain reduction, and elimination of necrotic tissue without requiring active debridement was achieved using Formulation 18. This dressing change protocol was significantly more economically effective than advanced impregnated dressings, while providing an appropriate environment for epithelization of the wound bed.

Example 35. The Use of Formulation 18 in the Treatment of Lower Leg Ulceration: Case Report A 70-year-old white man with a history of long-term smoking and DVT progressed to PE. Hospital course involved anticoagulation and IVF placement. Post-hospitalization, he developed bilateral lower leg venous ulcers and a low albumin level was diagnosed. Protein supplement was started along with aggressive dressing changes with honey sheets, unna boot, coban, and ace wrap performed twice a week progressing to weekly. Podiatry followed him twice a month for the acute phase. Albumin level normalized, dressing changes were continued with slow improvement, at which time acceptable healing had resulted and the patient was transitioned to compression stockings.

After one month of not wearing compression stockings, not elevating his extremities, and continuing to smoke, the patient developed a right lower leg ulcer. Given his history of slow healing, a trial of Formulation 18 was initiated. His albumin continued to be normal.

A thin layer of Formulation 18 was applied to and around the ulcer. A honey sheet was then applied followed by an unna boot, coban, and an ace wrap (for compression). This dressing was changed weekly. At each dressing change his leg was cleaned with saline.

After 4 weeks of weekly dressing changes utilizing Formulation 18, the ulcer was significantly smaller versus his prior history of slow healing. He transitioned back to compression stockings much faster.

A significant reduction in healing time was observed by including Formulation 18 versus not using Formulation 18 on this gentleman. His first ulcer was very slow to heal with the honey-only protocol (6-7 months); however, the addition of Formulation 18 with the same dressing technique on a second venous ulceration resulted in a dramatic reduction in healing time.

Example 36. The Use of Formulation Example 18 in the Treatment of a Pediatric Polymicrobial Infection: Case Report A 9-year-old boy with no significant medical history presented to clinic with an infected lesion to the left lateral chin. His father reports that the boy sustained a mechanical excoriation burn during karate when he fell on a mat. The parents treated the wound topically with bacitracin for 7 days and have noted a worsening of the erythema, edema, and topical warmth to the area with mild purulent drainage. The patient complained of tenderness to palpation. A culture, taken in office, revealed Herpes simplex type 1 and Methicillin Resistant *Staphylococcus aureus* (MRSA).

The patient was treated topically with Formulation Example 18. The patient's parents were instructed to wash the area gently with water and pat dry. The use of gloves was suggested due to the highly contagious nature of the infecting microorganisms. A thin layer of Formulation Example 18 was applied twice daily, morning and bedtime, and covered with a Band-Aid. The patient was given strict instructions to refrain from all sports until the infection abated.

The patient's parents reported by day two they the purulent drainage had ceased. The erythema and edema were resolving. By day 3 all edema and erythema had completely resolved. The patient was no longer tender to palpation. By day 7, the infection had completely resolved and the remaining eschar was beginning to loosen from the new epithelium.

The use of Formulation Example 18 is safe and effective for use on pediatric patient with polymicrobial skin infections. The petrol base is gentle on young skin and treats complicated infections. The ease of use is of particular importance in a pediatric population where swallowing medicines is often a challenge for caregivers. The aggressive treatment of infection in these highly communicable bacterial strains is an attractive feature of this product.

Example 37. The Use of Formulation Example 18 in the Treatment of Diaper Dermatitis: Case Report Irritant diaper dermatitis is a pervasive form of skin irritation commonly found in infants and toddlers. Prolonged exposure of the skin to irritants exacerbates these attacks. Such irritants include infrequent diaper changes, diarrhea, and contact allergy. The change in topical skin pH causes a breakdown in the epidermis, resulting in a painful erythematous rash to the most prominent areas of the buttocks.

The 4-month old patient was brought to his pediatrician by his parents after an acute onset of irritant diaper dermatitis. The patient exhibited a distressed affect, crying and avoiding pressure to the affect area. Upon physical exam, shiny erythematous raised patches were observed on the convex areas of the buttocks. Skin folds were spared. Parents reported that the rash has been present for 3 days and was worsening. Increased frequency in diaper changes had failed to improve symptoms. The patient had recently been experiencing diarrhea prior to onset which has now subsided.

The patient was assessed and the site of irritation was gently flushed with sterile water. The area was blotted dry and treated with topical application of Formulation Example 18 to the affected areas and surrounding tissue. A dry diaper was applied and the parents were given instructions for frequent diaper changes with gentle cleaning and application of Formulation Example 18 at each change.

Upon application the patient was noticeably more comfortable; the crying stopped and the patient began showing interest is a toy, indicating that the pain was subsiding. Twelve hours after the initial treatment the erythema had decreased by 85% and the parents reported that the child had resumed eating, playing, and was no longer fussy. After 18 hours a total resolution of the condition had been achieved.

The stratum corneum, the most superficial layer of skin, is comprised of keratinocytes and is thinner and especially sensitive in young pediatric patients. The third layer, the stratum granulosum, is a lipid producing layer which provides a hydrophobic barrier to the lesser skin layers thus providing a protective barrier to the irritant therefore the irritation is primarily contained to the first two epidermal layers. Formulation Example 18 has a petrolatum base and is naturally hydrophobic, thereby mimicking the body's natural defense mechanism and speeding healing to the affected area. The antimicrobial properties support the immune system and protect against common infections associated with severe diaper rash.

There are many treatments for irritant diaper dermatitis, the most common of which include zinc based creams, titanium dioxide jellies, anti-fungals, antacids, and corn starch. Research shows that the creams, jellies, and antacids are only minimally effective without application of a petrol layer. Anti-fungals are effective if the cause of the irritation is fungal in nature and often takes a 7-day course to achieve resolution. Lastly, corn starch is thought to prevent chaffing which minimizes discomfort but does not provide rapid relief from symptoms. Formulation Example 18 is currently the only product which has a petrolatum base that balances the pH of the skin and is capable of treating a polymicrobial infection.

A rapid rate of healing and pain resolution was achieved using Formulation Example 18. By providing a lipid bilayer, Formulation Example 18 aids the body's natural defenses to protect skin from pH induced breakdown with a medicated, water proof barrier thus both treating and protecting the skin simultaneously.

Example 38. Treatment of Non-Healing Abrasion with Formulation Example 18: Case Report Evidenced based protocols for the treatment of radiodermatitis is scarce and research indications that hospital management of these cases lacks consistency. A literature review in 2010 concluded that there was insufficient evidence to advocate for any one therapeutic option. In addition, a previous study reported an 80-90% incidence of erythematous reactions and a 10-15% incidence of moist desquamation in patients undergoing radiation therapy indicating this condition is a prevalent side effect to radiation therapy. Here, a case of radiodermatitis in which treatment with Formulation Example 18 was performed is reported.

A 54-year-old female had a history of a soft tissue sarcoma which had been successfully treated with radiation therapy, but consequently suffered an E3 Radiation-Induced Skin Reaction Assessment Scale (RISRAS) type radiodermatitis to the lateral aspect of her right lower extremity.

At 52 years, she experienced increased right distal leg pain and was referred to an oncologist where she was found to have a soft tissue sarcoma. After successful treatment of the sarcoma, which included adjuvant radiotherapy, she presented to the office with a 15.4 cm by 8.8 cm painful, solitary, erythematous plaque to the distal right lateral lower extremity consistent with radiodermatitis.

The occurrence rate of radiodermatitis in patients that underwent radiotherapy has been reported to be as high as 46% in one study. Side effects of this treatment results in increased occurrence of local skin lesions with possible ulceration, pain, and risk of infection.

The patient reported having been previously treated with hyaluronidase-based cream, sucralfate cream, biafine cream, and mepitel but was still experiencing pain and was displeased with the physical aesthetic of the wound. A thin layer of Formulation Example 18 was applied to and around the affected area. The area was covered with sterile telfa, wrapped with kerlix, and paper tape, taking care to avoid placing adhesive directly in contact with the skin. This dressing was changed twice daily. At each dressing change, the wound was cleaned with sterile saline.

A noticeable reduction in the erythema could be seen after one application and by the end of one week the plaque was almost totally resolved with only mild patchy spotting remaining. Patient reported that her pain had resolved completely and she was pleased with her outcome. In conclusion, Formulation Example 18 was found to be efficacious in treating radiodermatitis rapidly with no toxicity or side effects. The treatment was also economically efficacious. In future, randomized control trials will be established for further observation of Formulation Example 18 in treating radiation burns.

Example 39. Treatment of Wagner Grade 2 Ulceration with Formulation Example 18: Case Report A 72 year old man with cardiovascular disease and well-controlled diabetes mellitis presented to the clinic with an ulcer that had been present for 6 months. The ulcer measured 3.2 cm×1.9 cm×0.2 cm and was staged as a Wagner grade 2. He was married with 3 adult children, did not smoke, drank alcohol socially, and had a family history of various endocrine disorders. He denied previous ulcerations and attributed his ulcer to "a bug bite." Past treatment of his wound had included betadine, silvadene, and hydrogel to the wound bed. At time of presentation, he was applying silvadene every other day with a dry, sterile dressing, but wound measurements indicated poor healing. His medications were metformin, clopidogrel, metroprolol, low dose aspirin, and simvastatin with allergies to ACE inhibitors, penicillin, and sulfa drugs.

The patient presented for assessment of his diabetic ulcers and was found to have an ulcer on the lateral aspect of his calf. The wound base was 40:60 ratio fibrogranular with erythematous borders that extended 6 mm from the wound bed. Surrounding flesh was warm to the touch when compared to the contralateral side. It did not probe to bone, had no tracking, and exudate was moderate. A wound culture grew *Staphylococcus aureus* and pain was reported as 6/10.

Treatment began with mechanical debridement. Wound base was brought to bleeding and a thin layer of Formulation Example 18 was applied to the ulcer and surrounding tissue. The wound was dressed with a FiltreX bandage and this dressing was left in contact with the wound for 5 days. The patient was permitted to bathe while the FiltreX was in place, as it provides moisture protection. At day five, the home health nurse reported significant granulation and a reduction in the wound size from 3.2 cm×1.9 cm×0.2 cm to 2.1 cm×0.9 cm×0.05 cm.

Ten days into treatment revealed significant epithelialization of the wound bed. The wound measured 1.3 cm×0.4 cm. Depth was no longer measurable as the surrounding tissue had granulated in. The patient reported no further pain, erythema had resolved, and temperature returned to appropriate, indicating a resolution of the inciting infection. Dressing with Formulation Example 18 and FiltreX was continued for 10 more days at which time the wound was found to be completely resolved with full epithelialization of the wound and the formation of fibrous tissue.

Formulation Example 18 is an adjunctive therapy for chronic diabetic ulceration. The petrolatum base provides the moisture necessary for proper wound healing without macerating the wound. Furthermore, the non-cytotoxic, antimicrobial properties are conducive to rapid healing in that it allows for unimpeded fibroblastic activity to take place, thereby creating an ideal setting for the body's natural response to wound healing.

With respect to comfort, affordability, and ease of use, Formulation Example 18 was found to be the ideal treatment formula. The bandage, and subsequently Formulation Example 18, stays in contact with the wound for up to 7 days. This dressing endurance, both primary and secondary, is unique and minimizes the need for daily interruptions of the patient's life for dressing changes. Additionally, the bandage is hydrophobic which ensures the patient may bathe without concerns of dressing or wound disruption. This is a unique advantage due to the ability to shower making treatment more tolerable. In terms of patient compliance, the comfort and versatility of this dressing combination increases the likelihood that the patient will maintain a proper healing environment thereby leading to more successful outcomes. Ultimately, the combination of Formulation Example 18 and FiltreX provided the ideal environment for complete resolution of this difficult to heal diabetic ulcer.

Example 40. Treatment of Non-Healing Complicated Skin Tear with Formulation Example 18: Case Report Skin tears result from a separation of the two major layers of human skin, the epidermis and the dermis. They represent a major problem affecting older adults with prevalence rates between 14% and 24%. An 88 year old white female with a history of Alzheimer's, low albumin, PVD, hypertension, and hypothyroidism had been undergoing unsuccessful treatment for four months in an attempt to manage a complicated skin tear. Many dressing techniques had been attempted with minimal progress, including silver and topical antibiotics. A thin layer of Formula I was applied to and around the wound area. A non-adherent gauze sheet was then applied, followed by an ace wrap (for compression). This dressing was changed weekly. At each dressing change, her leg was cleaned with saline. Within weeks, the wound had stabilized, with complete epithelialization within two weeks. Notable healing can be seen and continues through week eleven. Moreover, while non-adherent regimens were always used, dressing changes were painful to the patient, indicated by visual and auditory responses to the removal of dressing materials from the wound site. While using Formulation Example 18 there was no discomfort/pain response during dressing changes. Formulation Example 18 added an additional, non-adherent layer of protection, decreasing discomfort while stimulating healing, ultimately resulting in re-epithelialization The use of Formulation Example 18 during the dressing change protocol stimulated healing, protected the site from additional physical insult, and reduced pain during dressing changes. For such non-ambulatory patients, risk of limb loss and infection is very high, and the healing of such a complicated, difficult wound represents a major success.

Example 41. Treatment of Phytophotodermatitis with Formulation Example 18: Case Report A 38-year-old woman with no significant medical history presented with a 2-day history of an erythematous vesiculobullous plaque with localized edema and erythema. She denied puritis, but admitted to associated burning sensation. Prior to the onset of the lesion, she went hiking near her home during which she picked oranges off of a tree she found. Upon examination, the patient has a central plaque measuring 4.1 cm×3.4 cm with interspersed vesicles/bullae which the patient admitted to draining at home. There are 2 secondary patches: one measuring 0.9 cm and the other 4 mm. The lesions are located on the left anterior shin. They are edematous and erythematous, but without appreciable temperature variation as compared to the contralateral side.

Based on the patient's presentation and recent exposure to citrus plants, she was diagnosed with phytophotodermatitis, a common dermatological condition resulting from contact with furocoumarins under direct sunlight. The result of this exposure causes a phototoxic inflammatory response to the localized area. A common defining feature of this clinical condition is the absence of puritis with the patient complaining of burning instead, which differentiates this from contact dermatitis. There are four species of plants that are known to contain furocoumarins: Apiaceae, Rutaceae, Moraceae, and Leguminosae. Members of Apiaceae include parsnip, celery, and parsley. Rutaceae includes citrus fruits, and is thus the likely culprit in the present case. Figs belong to the Moraceae family and lastly, Psoralea corylifolia belongs in Leguminosae family.

The course of this condition begins with the acute phase, which peaks at day 3 and can last 3-5 days. The more concerning aspect of this condition, from the patient standpoint, is the resultant hyperpigmentation which often persists for years. This condition most commonly affects areas that are exposed to the element, such as hands, arms, and lower legs, so patients tend to be distressed over the resultant physical deformity.

A thin layer of Formulation Example 18 was applied to the plaque and surrounding tissues. The area was covered with sterile telfa, wrapped with kerlix and paper tape, taking care to avoid placing adhesive directly in contact with the skin. This dressing was changed daily. At each dressing change, the wound was cleaned with sterile saline.

After 3 days of application, the acute phase resolved and the post-inflammatory hyperpigmentation set in. The patient continued with daily dressing changes and by 20 days of treatment, the hyperpigmentation was almost totally resolved with only mild patchy spotting remaining.

Formulation Example 18 was found to be efficacious in treating both the acute and post-inflammatory hyperpigmentation phases of phytophotodermatitis, the latter of which is known to often persist for years. In the future, it is recommended that randomized control trials be conducted with Formulation Example 18 to treat hyperpigmented lesions.

Example 42. Stability

Formulation Example 18 was packaged in tubes was subjected to an accelerated stability study. Formulation Example 18 was placed sideways in a 40° C.±2° C./75%±5% relative humidity (RH) storage chamber for different intervals to yield a period of three months. The product was assessed for physical and analytical characteristics. When stored at 40° C.±2° C./75%±5% (RH) benzyl alkonium chloride was stable as shown in Table 15.

TABLE 15

Accelerated Stability Testing

| Analytical Assay Testing | Specification | Initial: Assessing | 1 Month Assessing | 2 Months Assessing | 3 Months Assessing |
|---|---|---|---|---|---|
| Benzalkonium Chloride | 0.0071%-0.0086% 0.0081% | 0.0084% | 0.0085% | 0.0075% | 0.0086% |

Additionally, the product met specification for appearance, odor, specific gravity, viscosity and package compatibility at all time points tested.

Formulation Example 18 was also tested under for microbial counts at 40° C.±2° C./75%±5% were as shown below. The results are shown in Table 16.

TABLE 16

Accelerated Stability Testing

| Micro Testing | SPEC | Method | Results Initial Assessing | 1 Month Assessing | 2 Months Assessing | 3 Months Assessing |
|---|---|---|---|---|---|---|
| Total Plate Count (TPC) | <100 cfu/ml | TM-01 | <10 cfu/ml | <10 cfu/ml | <10 cfu/ml | <10 cfu/ml |
| Yeast/Mold | <100 cfu/ml | TM-01 | <10 cfu/ml | <10 cfu/ml | <10 cfu/ml | <10 cfu/ml |
| Enrichment (Pathogens) | Absent | Absent | Absent | Absent | Absent | Absent |
| *Pseudomonas* | Absent | Absent | Absent | Absent | Absent | Absent |
| *S. aureus* | Absent | Absent | Absent | Absent | Absent | Absent |
| *E. coli* | Absent | Absent | Absent | Absent | Absent | Absent |
| Coliforms | Absent | Absent | Absent | Absent | Absent | Absent |
| *Salmonella/Shigella* | Absent | Absent | Absent | Absent | Absent | Absent |

Additionally, the product met specification for appearance, odor, specific gravity, viscosity and package compatibility at all time-points tested when under standard conditions for over nine months.

Example 43. Effect of Formulation Example 18 on Bio-Burden in Live Wounds

Fresh wounds on eight patients were treated by applying a thin layer Formulation Example 18 to the wounds and surrounding tissue. The wounds were dressed with a pressure dressing, and this dressing was left in contact with the wound for one week. The wound was swabbed before treatment and then again at the conclusion of treatment when the dressing was removed after a week. Bio-burden analyses of the swab samples were performed for total microbial count and *Staphylococcus* count.

TABLE 17

Bio-burden analysis

| | Total Bacteria CFU/Swab | | *Staphylococcus* spp. CFU/Swab | |
|---|---|---|---|---|
| Sample ID | Pre | Post | Pre | Post |
| Patient 3 | $9.50 \times 10^3$ | $2.10 \times 10^2$ | $1.55 \times 10^4$ | <5.00 |
| Patient 4 | $3.40 \times 10^6$ | $1.87 \times 10^5$ | $2.70 \times 10^6$ | $2.15 \times 10^4$ |
| Patient 5 | $2.97 \times 10^5$ | 5.00 | $5.30 \times 10^2$ | <5.00 |
| Patient 6 | $5.50 \times 10^5$ | N/A | $3.51 \times 10^5$ | N/A |
| Patient 7 | $1.06 \times 10^7$ | $4.02 \times 10^5$ | $7.60 \times 10^6$ | $3.00 \times 10^5$ |
| Patient 8 | $6.32 \times 10^5$ | N/A | $2.60 \times 10^4$ | N/A |
| Patient 10 | $7.00 \times 10^6$ | N/A | $2.85 \times 10^4$ | N/A |
| Patient 11 | $3.25 \times 10^6$ | N/A | $1.60 \times 10^6$ | N/A |

The limit of detection for this assay was 5 CFU/Swab. The limit of detection for patient 3 was 10 CFU/Swab. Samples with no microbial recovery are reported as <5.00. Wounds that were completely healed within the seven day period were not swabbed after treatment and were marked N/A.

One week after treatment revealed significant reductions in total microbial counts and *staphylococcus* counts. This was especially apparent for the *staphylococcus* counts. In some instances, the wounds were healed within the seven day duration of the experiment, and therefore were not swabbed.

STATEMENTS OF THE DISCLOSURE

Statement 1: An oil-based composition for the treatment or dressing of a wound, the composition comprising: an oil-based carrier; a polar solvent comprising one or more polar antimicrobial agents; collagen or a collagen-based material; wherein the polar solvent comprising one or more polar antimicrobial agents is suspended in the oil-based carrier.

Statement 2: The composition according to Statement 1, wherein the collagen or collagen-based material is suspended in the oil-based carrier.

Statement 3: The composition according to Statement 1, wherein the polar solvent comprising one or more antimicrobial agents and/or the collagen or collagen-based material does not separate from the oil-based carried for at least 6 months.

Statement 4: The composition according to Statement 1 or Statement 2, wherein the collagen or collagen-based material is in powdered form.

Statement 5: The composition according to Statement 1 or Statement 2, wherein the collagen or collagen-based material is micronized collagen.

Statement 6: The composition according to any one of the preceding Statements 1-5, where in the collagen or collagen-based material is characterized by an average particle size of from about 5 microns to about 80 microns.

Statement 7: The composition according to any one of the preceding Statements 1-5, where in the collagen or collagen-based material is characterized by an average particle size of from about 20 microns to about 70 microns.

Statement 8: The composition according to any one of the preceding Statements 1-5, where in the collagen or collagen-based material is characterized by an average particle size of from about 5 microns to about 30 microns.

Statement 9: The composition according to any one of the preceding Statements 1-5, where in the collagen or collagen-based material is characterized by an average particle size of from about 10 microns to about 30 microns.

Statement 10: The composition according to any one of the preceding Statements 1-5, where in the collagen or collagen-based material is characterized by an average particle size of from about 15 microns to about 30 microns.

Statement 11: The composition according to any one of the preceding Statements 1-5, where in the collagen or collagen-based material is characterized by a particle size of less than 20 microns.

Statement 12: The composition according to any one of the preceding Statements 1-5, where in the collagen or collagen-based material is characterized by an average particle size of less than 20 microns.

Statement 13: The composition according to any one of the preceding Statements 1-5, where in the collagen or collagen-based material is characterized by an average particle size of less than 30 microns.

Statement 14: The composition according to any one of the preceding Statements 1-7, where in the collagen or collagen-based material comprises a material selected from the group consisting of extracellular matrix materials, micronized extracellular matrix, purified collagen, Type I collagen, Type II collagen, Type III collagen, Type X collagen, collagen fibers, collagen fibrils, micronized collagen, defibrillated collagen, coarse collagen bundles, non-cross-linked collagen, non-mineralized collage, collagen treated to control cross-linking (e.g., via chemical, thermal, photo, or radiation-induced cross-linking), collagen-glycosaminoglycan (GAG) mixtures, and any combination thereof.

Statement 15: The composition according to any one of the preceding Statements 1-14, wherein the collagen or collagen-based material comprises from about 5 wt % to about 35 wt % of the oil-based composition.

Statement 16: The composition according to any one of the preceding Statements 1-14, wherein the collagen or collagen-based material comprises from about 5 wt % to about 25 wt % of the oil-based composition.

Statement 17: The composition according to any one of the preceding Statements 1-14, wherein the collagen or collagen-based material comprises from about 5 wt % to about 20 wt % of the oil-based composition.

Statement 18: The composition according to any one of the preceding Statements 1-14, wherein the collagen or collagen-based material comprises from about 5 wt % to about 15 wt % of the oil-based composition.

Statement 19: The composition according to any one of the preceding Statements 1-14, wherein the collagen or collagen-based material comprises from about 15 wt % to about 30 wt % of the oil-based composition.

Statement 20: The composition according to any one of the preceding Statements 1-19, wherein the oil-based based carrier is selected from the group consisting of animal oil, vegetable oil, natural oil, synthetic oil, hydrocarbon oils, silicone oils, and semi-synthetic derivatives thereof, and any combination thereof.

Statement 21: The composition according to any one of the preceding Statements 1-19, wherein the oil-based based carrier is selected from the group consisting of is selected from the group consisting of mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, C12-15 alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, *eucalyptus* leaf oil, lemon grass leaf oil, *melaleuca* leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, *cassia* Bark oil, cinnamon bark oil, *sassafras* Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combination thereof.

Statement 22: The composition according to any one of the preceding Statements 1-19, wherein the oil-based based carrier is coconut oil.

Statement 23: The composition according to any one of the preceding Statements 1-19, wherein the oil-based based carrier is petrolatum.

Statement 24: The composition according to Statement 23, wherein the composition comprises greater than about 60% by weight petrolatum.

Statement 25: The composition according to Statement 23, wherein the composition comprises greater than about 70% by weight petrolatum.

Statement 26: The composition according to Statement 23, wherein the composition comprises greater than about 80% by weight petrolatum.

Statement 27: The composition according to Statement 23, wherein the composition comprises greater than about 90% by weight petrolatum.

Statement 28: The composition according to any one of the preceding Statements 1-27, wherein the polar solvent is water.

Statement 29: The composition according to any one of the preceding Statements 1-27, wherein the polar solvent is ethanol.

Statement 30: The composition according to any one of the preceding Statements 1-27, wherein the polar solvent is a mixture of water and ethanol.

Statement 31: The composition according to any one of the preceding Statements 1-30, wherein the polar solvent comprises ascetic acid.

Statement 32: The composition according to any one of the preceding Statements 1-31, wherein the one or more polar antimicrobial agents comprises polyhexamethylene biguanide (PHMB).

Statement 33: The composition according to Statement 32, wherein the composition comprises from about 0.1% to about 1% by weight PHMB.

Statement 34: The composition according to Statement 32, wherein the composition comprises from about 0.05% to about 5% by weight PHMB.

Statement 35: The composition according to Statement 32, wherein the composition comprises from about 0.05% to about 3% by weight PHMB.

Statement 36: The composition according to Statement 32, wherein the composition comprises from about 0.2% to about 0.6% by weight PHMB.

Statement 37: The composition according to Statement 32, wherein the composition comprises from about 0.3% to about 0.5% by weight PHMB.

Statement 38: The composition according to Statement 32, wherein the composition comprises from about 0.1% to about 3.5% by weight PHMB.

Statement 39: The composition according to Statement 32, wherein the composition comprises from about 0.05% to about 2.5% by weight PHMB.

Statement 40: The composition according to Statement 32, wherein the composition comprises from about 0.5% to about 3% by weight PHMB.

Statement 41: The composition according to Statement 32, wherein the composition comprises from about 0.5% to about 2.5% by weight PHMB.

Statement 42: The composition according to Statement 32, wherein the composition comprises from about 1.5% to about 2.5% by weight PHMB.

Statement 43: The composition according to any one of the preceding Statements 1-42, wherein the one or more polar antimicrobial agents comprises a cationic biocide.

Statement 44: The composition according to Statement 43, wherein the cationic biocide is selected from the group consisting of benzalkonium chloride, cetrimide, chlorhexidine, polihexanide biguanide (polihexanide, polyhexamethylene biguanide, polyhexamethylene guanide, poly(imino-imidocarbonyl-iminoimidocarbonyl-iminohexamethylene), poly(hexamethylenebiguanide), polyaminopropyl biguanide), and salts or combinations thereof.

Statement 45: The composition according to any one of the preceding Statements 1-44, wherein the polar solvent further comprises a preservative selected from the group consisting of benzalkonium chloride, cetrimide, chlorhexidine, and any combination thereof.

Statement 46: The composition according to any one of the preceding Statements 1-45, wherein the composition comprises from about 0.001% to about 0.15% by weight benzalkonium chloride (BZK).

Statement 47: The composition according to any one of the preceding Statements 1-45, wherein the composition comprises from about 0.001% to about 0.01% by weight or from about 0.005% to about 0.007% by weight benzalkonium chloride (BZK).

Statement 48: The composition according to any one of the preceding Statements 1-47, further comprising one or more therapeutic agents selected from the group consisting of stem cells, TGF-alpha, TGF-beta (TGFβ1, TGFβ2, TGFβ3), platelet-derived growth factor (PDGF), epidermal growth factor (EGF), fibroblast growth factor also referred to as keratinocyte growth factor (FGF1, FGF2, FGF4, FGF7), vascular endothelial growth factor (VEGF), insulin-like growth factor (IGF), connective tissue growth factor (CTGF), activin, interleukin-1 (IL1α, IL1β), TNFα, GM-CSF, a powdered antibiotic, an antifungal agent, a hemostatic agent, cytokines, and hyaluronic acid.

Statement 49: The composition according to any one of the preceding Statements 1-48, wherein the composition contains no emulsifier.

Statement 50: The composition according to any one of the preceding Statements 1-48, wherein the composition excludes an added emulsifier.

Statement 51: The composition according to any one of the preceding Statements 1-48, wherein the composition excludes an added emulsifier other than the recited components.

Statement 52: The composition according to any one of the preceding Statements 1-51, wherein the composition is a topical composition for application to the wound of a subject in need thereof.

Statement 53: The composition according to any one of the preceding Statements 1-52, wherein the composition is an ointment.

Statement 54: The composition according to any one of the preceding Statements 1-53, wherein the composition is a cream.

Statement 55: The composition according to any one of the preceding Statements 1-54, wherein the composition is prepared by a process comprising: a) dissolving the one or more polar antimicrobial agents in a polar solvent to give an antimicrobial agent solution; b) heating the oil-based carrier to a temperature sufficient to cause the oil-based carrier to melt or to a temperature sufficient to provide a oil-based carrier density capable of suspending a powdered collagen or a powdered collagen-based material, resulting in a melted oil-based carrier; c) mixing a powdered collagen or a powdered collagen-based material into the melted oil-based carrier to give a suspended collagen oil-based carrier composition; d) heating the antimicrobial agent solution to a temperature higher than the temperature of the melted oil-based carrier to give a heated antimicrobial solution; e) mixing the suspended collagen oil-based carrier composition and the heated antimicrobial solution to give a melted mixture; and f) cooling the melted mixture to give the oil-based composition.

Statement 56: The composition according to Statement 55, wherein the heated antimicrobial solution has a temperature that is about 1° C. to about 5° C. higher than the temperature of the suspended collagen oil-based carrier composition at the time of mixing.

Statement 57: A method of treating or dressing a wound in a subject, the method comprising applying the composition according to any one of the preceding Statements 1-56 to a wound in need of dressing or treatment.

Statement 58: A method of treating or dressing a post-surgical wound, the method comprising applying the composition according to any one of the preceding Statements 1-56 to a post-surgical wound in need of dressing or treatment.

Statement 59: A method of treating or dressing a skin graft post-surgery in a subject in need thereof, the method comprising applying the composition according to any one of the preceding Statements 1-56 to a post-surgical skin graft in need of dressing or treatment.

Statement 60: The method according to any one of the preceding Statements 57-59, further comprising covering the composition with a wound covering selected from the group consisting of a bandage, wrap, gauze, sponge, and film, following the application of the composition to the wound or graft in need of treatment.

Statement 61: The method according to any one of the preceding Statements 57-59, further comprising: contacting the composition according to any one of claims 1-56 to a wound covering, wherein the wound covering is a selected from the group consisting of a bandage, wrap, gauze, sponge, and film; and applying the wound covering to the wound or graft in need of treatment.

Statement 62: The method according to any one of the preceding Statements 57-59, further comprising: impregnating a wound covering with the composition according to any one of the preceding Statements 1-56, wherein the wound covering is a selected from the group consisting of a bandage, wrap, gauze, sponge, and film; and applying the wound covering to the wound or graft in need of treatment.

What is claimed is:

1. An oil-based composition for the treatment or dressing of a wound, the composition comprising:
    an oil-based carrier;
    a polar solvent comprising one or more polar antimicrobial agents, wherein the polar solvent comprising one or more polar antimicrobial agents is suspended in the oil-based carrier; and
    powdered collagen or a powdered collagen-based material, wherein the powdered collagen or powdered collagen-based material is suspended in the oil-based carrier,
    wherein the oil-based carrier comprises petrolatum, the petrolatum comprising greater than about 60% by weight of the oil-based composition;
    wherein the polar solvent is selected from the group consisting of water, ethanol, a mixture of water and ethanol, ascetic acid, and any combination thereof; and
    wherein the powdered collagen or powdered collagen-based material comprises from about 5 wt % to about 35 wt % of the oil-based composition.

2. The composition according to claim 1, wherein the polar solvent comprising one or more antimicrobial agents and/or the powdered collagen or powdered collagen-based material does not separate from the oil-based carrier for at least 6 months.

3. The composition according to claim 1, wherein the powdered collagen or powdered collagen-based material is characterized by an average particle size of from about 5 microns to about 80 microns.

4. The composition according to claim 1, where in the powdered collagen or powdered collagen-based material comprises a material selected from the group consisting of extracellular matrix materials, micronized extracellular matrix, purified collagen, Type I collagen, Type II collagen, Type III collagen, Type X collagen, collagen fibers, collagen fibrils, micronized collagen, defibrillated collagen, coarse collagen bundles, non-crosslinked collagen, non-mineralized collage, collagen treated to control cross-linking, collagen-glycosaminoglycan (GAG) mixtures, and any combination thereof.

5. The composition according to claim 1, wherein the oil-based carrier further comprises one or more selected from the group consisting of animal oil, vegetable oil, natural oil, synthetic oil, hydrocarbon oils, silicone oils, and semi-synthetic derivatives thereof, and any combination thereof.

6. The composition according to claim 1, wherein the oil-based carrier further comprises one or more selected from the group consisting of mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Decyl oleate, diisopropyl adipate, C12-15 alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, *eucalyptus* leaf oil, lemon grass leaf oil, *melaleuca* leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, *cassia* Bark oil, cinnamon bark oil, *sassafras* Bark oil, camphor wood oil, cedar wood oil, rosewood oil, sandalwood oil, rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combination thereof.

7. The composition according to claim 1, wherein the oil-based based carrier further comprises coconut oil.

8. The composition according to claim 1, wherein the composition comprises greater than about 80% by weight petrolatum.

9. The composition according to claim 1, wherein the one or more polar antimicrobial agents comprises polyhexamethylene biguanide (PHMB).

10. The composition according to claim 9, wherein the composition comprises from about 0.05% to about 5% by weight PHMB.

11. The composition according to any to claim 1, wherein the one or more polar antimicrobial agents comprises a cationic biocide.

12. The composition according to claim 11, wherein the cationic biocide is selected from the group consisting of benzalkonium chloride, cetrimide, chlorhexidine, polihexanide biguanide, and salts or combinations thereof.

13. The composition according to claim 1, wherein the polar solvent further comprises a preservative selected from the group consisting of benzalkonium chloride, cetrimide, chlorhexidine, and any combination thereof.

14. The composition according to claim 1, wherein the composition comprises from about 0.001% to about 0.15% by weight benzalkonium chloride (BZK).

15. The composition according to claim 1, wherein the composition excludes an added emulsifier other than the recited components.

16. The composition according to claim 1, wherein the composition is a topical cream or ointment for application to the wound of a subject in need thereof.

17. The composition according to claim 1, wherein the composition is prepared by a process comprising:
    a) dissolving the one or more polar antimicrobial agents in a polar solvent to give an antimicrobial agent solution;
    b) heating the oil-based carrier to a temperature sufficient to cause the oil-based carrier to melt or to a temperature sufficient to provide a oil-based carrier density capable of suspending a powdered collagen or a powdered collagen-based material, resulting in a melted oil-based carrier;

c) mixing a powdered collagen or a powdered collagen-based material into the melted oil-based carrier to give a suspended collagen oil-based carrier composition;

d) heating the antimicrobial agent solution to a temperature higher than the temperature of the melted oil-based carrier to give a heated antimicrobial solution;

e) mixing the suspended collagen oil-based carrier composition and the heated antimicrobial solution to give a melted mixture; and f) cooling the melted mixture to give the oil-based composition.

18. The composition according to claim 17, wherein the heated antimicrobial solution has a temperature that is about 1° C. to about 5° C. higher than the temperature of the suspended collagen oil-based carrier composition at the time of mixing.

19. A method of treating or dressing a wound or a post-surgical skin graft in a subject, the method comprising applying the composition according to claim 1 to a wound or post-surgical skin graft in need of dressing or treatment.

20. The method according to claim 19, further comprising:

contacting the composition according to claim 1 to a wound covering, wherein the wound covering is a selected from the group consisting of a bandage, wrap, gauze, sponge, and film; and applying the wound covering to the wound or post-surgical skin graft in need of treatment.

* * * * *